United States Patent [19]

Baldwin et al.

[11] Patent Number: 5,334,591

[45] Date of Patent: Aug. 2, 1994

[54] TRICYCLIC THIENOTHIOPYRAN CARBONIC ANHYDRASE INHIBITORS

[75] Inventors: John J. Baldwin, Gwynedd Valley; Kenneth L. Shepard, North Wales; Gerald S. Ponticello, Lansdale; Theresa M. Williams, Harleysville, all of Pa.

[73] Assignee: Merck & Co., Inc., Rahway, N.J.

[21] Appl. No.: 26,363

[22] Filed: Mar. 4, 1993

Related U.S. Application Data

[63] Continuation-in-part of Ser. No. 777,812, Oct. 15, 1991, abandoned.

[51] Int. Cl.5 ............... C07D 471/18; C07D 487/18; A61K 31/44; A61K 31/55
[52] U.S. Cl. ............................. 514/215; 514/291; 514/411; 540/581; 546/80; 548/430; 548/431
[58] Field of Search ............... 548/430, 431; 546/80; 540/581; 514/215, 291, 411

[56] References Cited

U.S. PATENT DOCUMENTS

| | | | |
|---|---|---|---|
| 4,619,939 | 10/1985 | Maren | 514/363 |
| 4,677,115 | 6/1987 | Baldwin et al. | 514/432 |
| 4,797,413 | 1/1989 | Baldwin et al. | 514/432 |
| 5,175,284 | 12/1992 | Baldwin et al. | 540/581 |

*Primary Examiner*—Alan L. Rotman
*Attorney, Agent, or Firm*—Sylvia A. Ayler; Mark R. Daniel; Joseph F. DiPrima

[57] ABSTRACT

Conformationally constrained tricyclic thienothiopyran compounds are topically effective carbonic anhydrase inhibitors useful in the treatment of ocular hypertension and glaucoma associated therewith.

10 Claims, No Drawings

TRICYCLIC THIENOTHIOPYRAN CARBONIC ANHYDRASE INHIBITORS

This is a continuation-in-part of copending application, Ser. No. 07/777,812 filed Oct. 15, 1991, now abandoned.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. Many of these agents, however, also have other characteristics, e.g. membrane stabilizing activity, that are not acceptable for chronic ocular use. (S)-1-tert-Butylamino[(4-morpholino-1,2,5-thiadiazol-3-yl)-oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. Benzothiophene-2-sulfonamides, benzenesulfonyl-thiophene-2-sulfonamides, and thieno[2,3-b]thiopyran-2-sulfonamides are also reported to be carbonic anhydrase inhibitors topically effective in reducing intraocular pressure in U.S. Pat. Nos. 4,668,697; 4,585,787; and 4,797,413, respectively.

U.S. Pat. No. 4,619,939 discloses a process and composition for reducing intraocular pressure and reducing aqueous humor formation by applying topically to the cornea an effective mount of an aqueous solution of a carbonic anhydrase inhibitor having the following properties:

a. sufficiently soluble in water to form at least a 3 mM solution at pH 8.2 or a pKa of not greater than 7.3;
b. ether partition coefficient of at least 1.0;
c. chloroform partition coefficient of at least 0.01;
d. dissociation constant against carbonic anhydrase of not more than $3 \times 10^{-8}$ molar;
e. first order rate constant for penetration of the sulfonamide through a living rabbit cornea of at least 0.005 $hr^{-1}$;
f. not injurious to the cornea; and
g. stable in aqueous solution and in contact with the cornea.

OBJECTS OF THE INVENTION

It is an object of the present invention to provide new compounds that are effective in treating ocular hypertension and glaucoma associated therewith. Another object is to provide a method of treating a subject having ocular hypertension and glaucoma. A further object is to provide pharmaceutical formulations for administering these compounds. These and other objects of the present invention will be apparent from the following description.

SUMMARY OF THE INVENTION

This invention relates to conformationally constrained tricyclic thienothiopyrans of the structural formula

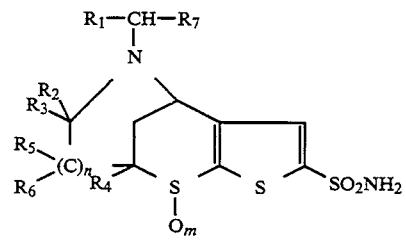

wherein $R_1$ is H, unsubstituted or substituted lower alkyl, lower alkenyl, aryl or aralkyl wherein the aryl groups are substituted by lower alkyl, halogen, $CF_3$, OH, lower alkyl-S(O)$_m$, or lower alkoxy; $R_2$, $R_3$, $R_5$, $R_6$ and $R_7$ are independently H or alkyl, or $R_2$ and $R_3$ together are =O; $R_4$ is H, lower alkyl, lower alkenyl, lower alkenyloxy or lower alkyl substituted by hydroxy, alkoxy, hydroxyalkoxy, alkoxyalkoxy, hydroxyalkoxyalkoxy, alkylamino, hydroxyalkylamino, alkoxyalkylamino, hydroxyalkoxyalkylamino, alkyl-S(O)$_m$, hydroxyalkyl-S(O)$_m$, alkoxyalkyl-S(O)$_m$, hydroxyalkoxyalkyl-S(O)$_m$, alkyl-S(O)$_m$alkoxy, hydroxyalkyl-S(O)$_m$alkoxy, alkyl-S(O)$_m$alkyl-S(O)$_m$, and hydroxyalkyl-S(O)$_m$alkyl-S(O)$_m$, and m and n are independently 0, 1, or 2.

This invention also relates to ophthalmic formulations comprising at least one of the novel compounds as active ingredient either alone or in combination with other ophthalmic medicaments such as pilocarpine, timolol or enaliprilat.

The invention also relates to a method of treating ocular hypertension and glaucoma associated therewith which comprises the topical ocular administration of a novel compound of this invention to a patient in need of such treatment.

DETAILED DESCRIPTION OF THE INVENTION

The novel compounds of the present invention have the structural formula:

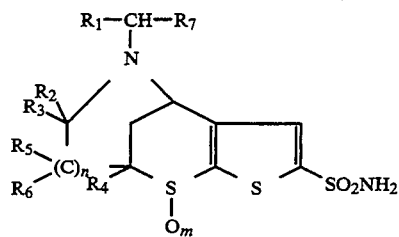

having a cis configuration, the enantiomers and mixtures thereof, or an ophthalmologically acceptable salt thereof wherein:

$R_1$ is
1) H;
2) $C_{1-6}$alkyl, $C_{1-6}$alkenyl or $C_{1-6}$alkyl substituted with F, OH, $C_{1-5}$alkylS(O)$_m$ or $C_{1-5}$alkyl-O—;
3) aryl or aralkyl wherein the aryl groups optionally are substituted by $C_{1-3}$-alkyl, halogen, $CF_3$, OH, or $C_{1-3}$alkoxy;

$R_2$, $R_3$, $R_5$, $R_6$, and $R_7$ are independently H or lower alkyl, preferably $C_{1-4}$alkyl, or $R_2$ and $R_3$ together are =O; and $R_4$ is 1) H, lower alkyl, preferably $C_{1-6}$;
2) $C_{1-6}$alkyl substituted with
  a) hydroxy,
  b) $C_{1-3}$alkyl-O—,
  c) hydroxy$C_{1-3}$alkyl-O—,
  d) $C_{1-3}$alkyl-O—$C_{1-3}$alkyl-O—,
  e) hydroxy$C_{1-3}$alkyl-O—$C_{1-3}$alkyl-O—,
  f) ($C_{1-3}$alkyl)$_2$N—,
  g) hydroxy$C_{1-3}$alkylNH—,
  h) $C_{1-3}$alkyl-O—$C_{1-3}$alkylNH—;
  i) hydroxy$C_{1-3}$alkyl-O—$C_{1-3}$alkylNH—;
  j) $C_{1-3}$alkyl-S(O)$_m$,
  k) hydroxy$C_{1-3}$alkyl-S(O)$_m$,
  l) $C_{1-3}$alkyl-O—$C_{1-3}$alky-S(O)$_m$,
  m) hydroxy$C_{1-3}$alkyl-O—$C_{1-3}$alkyl-S(O)$_m$,
  n) $C_{1-3}$alkyl-S(O)$_m C_{1-3}$alkyl-O—,
  o) hydroxy$C_{1-3}$alkyl-S(O)$_m C_{1-3}$alkyl-O—,
  p) $C_{1-3}$alkyl-S(O)$_m C_{1-3}$alkyl-S(O)$_m$,—
  q) hydroxy$C_{1-3}$alkyl-S(O)$_m C_{1-3}$alkyl-S(O)$_m$,
3) $C_{2-6}$alkenyl or $C_{2-6}$alkenyloxy; and m and n are independently 0, 1 or 2.

Preferred compounds of the present invention are those wherein $R_1$, $R_2$, $R_3$, $R_5$ and $R_6$ are independently H or $C_{1-6}$alkyl, and $R_4$ is H, $C_{1-6}$alkyl or $C_{1-6}$alkyl substituted by hydroxy, alkoxy, hydroxyalkoxy, alkoxyalkoxy, alkylamino, alkoxyalkylamino, alkyl-S(O)$_m$—, hydroxy$C_{1-3}$alkyl-S(O)$_m$—, $C_{1-3}$alkyl-S(O)$_m$—$C_{1-3}$alkyl-S(O)$_m$—, $C_{1-3}$alkyl-O—$C_{1-3}$alkyl-S(O)$_m$—, $C_{1-3}$alkyl-S(O)$_m$-$C_{1-3}$alkyl-O—, or $C_{2-6}$alkenyl or $C_{2-6}$alkenyloxy, and m and n are independently 0,1 or 2.

Most preferred compounds are
4-ethyl-2-[2-(2-methoxyethoxy)ethyl]-2,3,4,5-tetrahydro-2,5-methanothieno[3,2-f]-1,4-thiazepine-7-sulfonamide-1,1dioxide hydrochloride,
5-(4-methoxybenzyl)-2-methyl-3,4,5,6-tetrahydro-2H-2,6-methanothieno[3,2-g]-1,5-thiazocine-8-sulfonamide-1,1-dioxide,
5-(4-methoxybenzyl)-2-methoxypropyl-3,4,5,6-tetrahydro-2H-2,6-methanothieno[3,2-g]-1,5-thiazocine-8-sulfonamide-1,1-dioxide,
2-methyl-3,4,5,6-tetrahydro-2H-2,6-methanothieno[3,2-g]-1,5-thiazocine-8-sulfonamide-1,1-dioxide hydrochloride,
5-isobutyl-4-oxo-3,4,5,6-tetrahydro-2H-2,6-methanothieno[3,2-g]-1,5-thiazocine-8-sulfonamide,
5-isobutyl-4-oxo-3,4,5,6-tetrahydro-2H-2,6-methanothieno[3,2-g]-1,5-thiazocine-8-sulfonamide-1,1-dioxide,
5-isobutyl-3,4,5,6-tetrahydro-2H-2,6-methano-thieno-[3,2-g]-1,5-thiazocine-8-sulfonamide-1,1-dioxide hydrochloride,
5-propyl-3,4,5,6-tetrahydro-2H-2,6-methano-thieno[3,2-g]-1,5-thiazocine-8-sulfonamide-1,1-dioxide hydrochloride,
2,5-methanothieno[3,2-f]-1,4-thiazepine-7-sulfonamide-4-propyl-2,3,4,5-tetrahydro-1,1-dioxide hydrochloride and cis(S,S)2,5-methanothieno[3,2-f]-1,4-thiazepine-7-sulfonamide-4-ethyl-2,3,4,5-tetrahydro-1,1-dioxide hydrochloride.

The compounds of the present invention can be prepared by treating a compound of formula 1 with lithium bis(trialkylsilyl)amide, preferably lithium bis(trimethylsilyl)amide, in a polar solvent such as, for example, tetrahydrofuran (THF), for from about 5 minutes to about one hour under an inert atmosphere, for example, nitrogen, at lowered temperature of from about −100° C. to about −50° C., followed by treatment with N,N-dialkylmethylammonium iodide, preferably N,N-dimethylmethylammonium iodide, while permitting the temperature to rise from about 5° C. to about 25° C. The compound of formula 2 is recovered and a

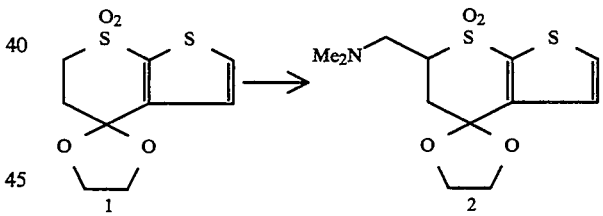

mixture of it and an alkyl iodide, preferably methyl iodide, is stirred at about ambient temperature for about 24 hours, dissolved in a polar solvent such as, for example, acetonitrile, and treated with 1,8-diazabicyclo-[5.4.0]undec-7-ene to give the product of formula 3.

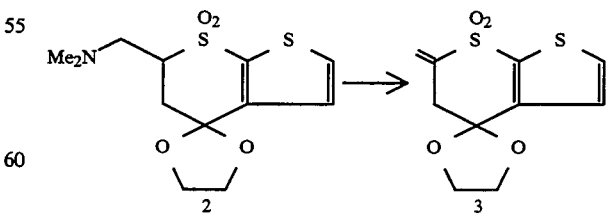

Sodium methanethiolate is added to a mixture of the compound of formula 3 and a polar solvent such as, for example, THF. After from about 5 minutes to about 2 hours, the solvent is removed, preferably in vacuo, to yield the compound of formula 4.

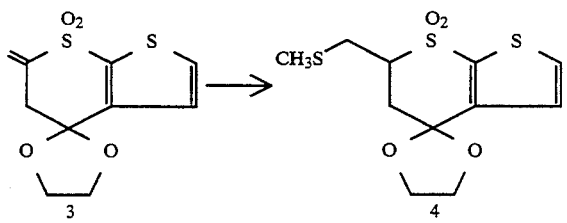

A solution of the compound of formula 4 in acid, preferably HCl, and a polar solvent, for example, THF, is heated to reflux for from about 10 minutes to about 2 hours after which the solvent is removed, preferably under reduced pressure, to yield the compound of formula 5.

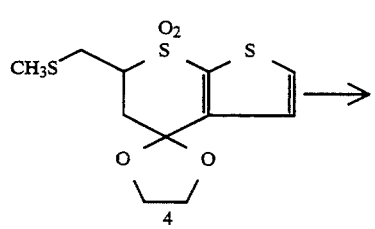

Sodium borohydride is added to a solution of the compound of formula 5 in an alcoholic solvent, for example, ethanol, methanol, THF or dioxane and the resulting mixture is stirred for about 5 minutes to about 2 hours. After cooling the reaction mixture to a temperature from about 15° C. to about −10° C., mineral acid, preferably HCl, is added to destroy excess sodium borohydride and the alcohol is removed, preferably under reduced pressure, to yield the compound of formula 6.

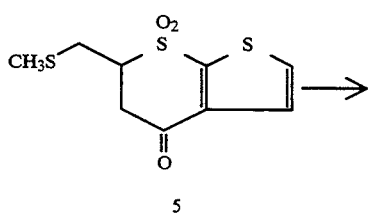

A tertiary mine, for example, a trialkylamine, preferably triethylamine, is added to a stirred solution of the compound of formula 6 and methanesulfonic anhydride in a polar solvent such as, for example, THF. After about one hour at about ambient temperature, the volatiles are removed, preferably under reduced pressure, to yield the compound of formula 7.

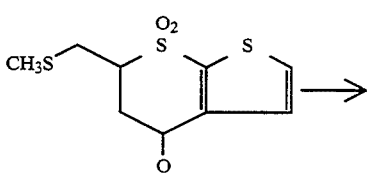

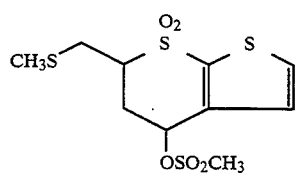

A mixture of sodium azide and the compound of formula 7 in dimethylsulfoxide (DMSO) is stirred at about ambient temperature for about 10 to about 30 hours to yield the product of formula 8.

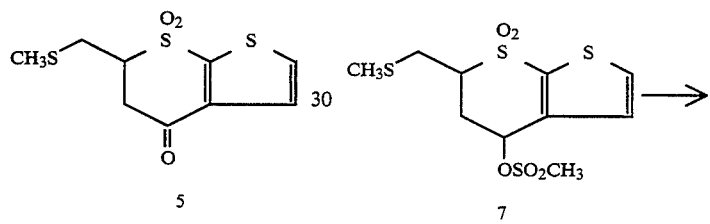

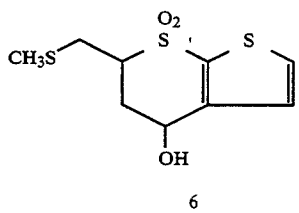

A mixture of the compound of formula 8 and triphenylphosphine in a polar solvent, for example, THF, is stirred at about ambient temperature for about 20 minutes to about 5 hours. An aldehyde of formula $R_1CHO$ wherein $R_1$ has the same meaning as defined previously, is added and stirring is continued for about 10 hours to about 30 hours. The resulting solution is added to a suspension of sodium borohydride in an alcohol, preferably ethanol, at a lowered temperature from about 15° C. to about −15° C. and stirred for about 10 minutes to about 3 hours. Excess sodium borohydride is destroyed by the addition of mineral acid, for example, HCl to give the compound of formula 9. To prepare compounds of formula 9 wherein $R_7$ is other than H, to the generated amine from the previous step is added a tertiary amine such as triethylamine or pyridine followed by a compound of formula $R_1CHX$
$R_7$,
wherein $R_1$ and $R_7$ have the meaning defined previously and X is halide, followed by stirring for about 10 hours to about 30 hours. The reaction mixture is then poured into a basic solution such as $NaHCO_3$ and aqueous hydroxide followed by extraction with an organic solvent such as diethyl ether, ethyl acetate, methylene chloride or chloroform.

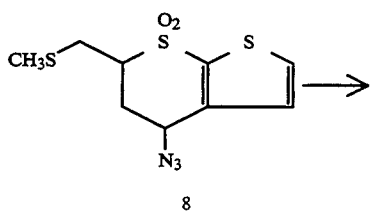

8

A solution of the compound of formula 9 in aqueous alkali such as, for example, NaOH, KOH, LiOH or NH₄OH, and THF is heated to reflux for about 0.5 hour to about 5 hours to give the compound of formula 10.

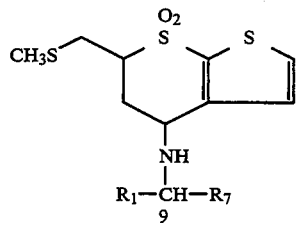

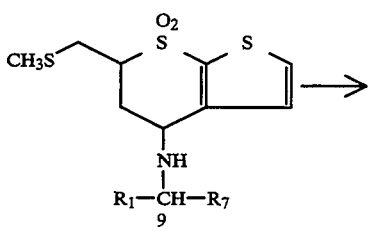

A solution of lithium bis(trialkylsilyl)amide, preferably, lithium bis(trimethylsilyl)amide, in a nonpolar solvent such as, for example, hexane, or in a polar solvent such as, for example, THF, is added to a stirred solution of the compound of formula 10 and a compound of formula R₄X wherein X is a halide, preferably bromine, and R₄ has the meaning defined previously. Specific examples of compounds of the formula R₄X are methyl bromide, methoxypropyl bromide, methylthioethyl bromide, 2-(2-methoxyethoxy)ethyl bromide or 2-(2-methylthioethylthio)ethyl bromide, in a polar solvent such as, for example, THF at lowered temperatures, typically at from about −0° C. to about −100° C., preferably at about −78° C., to give the compound of formula 11. When R₄ contains a sulfur atom, the corresponding sulfoxide or sulfone analogues can be prepared by standard oxidative procedures such as, for instance, those described for the preparation of the compounds of formulas 17 and 19.

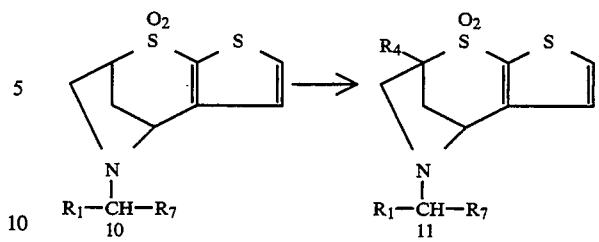

A solution of alkyl lithium, preferably butyl lithium, in a nonpolar solvent such as, for example, hexane is added to a solution of the compound of formula 11 in a polar solvent such as, for example, THF, at lowered temperatures, typically from about −50° C. to about −100° C., preferably at about −78° C. After from about 10 minutes to about 2 hours at this temperature, SO₂ is introduced over the surface of the cold stirred mixture for from about 1 minute to about 10 minutes. The solvent is removed under reduced pressure and the residue is dissolved in an alkali metal solution, preferably sodium acetate hydrate, and hydroxylamine-O-sulfonic acid is added, and the resulting reaction mixture is stirred for about 3 hours to about 15 hours at about ambient temperature. The mixture is then adjusted to about pH 7.5 by addition of alkali, preferably NH₄OH, to give the compound of formula 12.

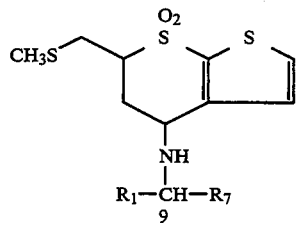

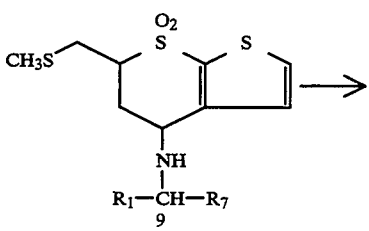

Alternatively, compounds of formula 14 can be prepared by heating at from about 50° C. to about 100° C. in the presence of base, such as LiOH, KOH, NaOH or NH₄OH in H₂O, compounds of formula 13 where X is CH₃S—, CH₃O—, CH₃OCH₂CH₂O—, +N(CH₃)₃, or any other leaving group.

-continued

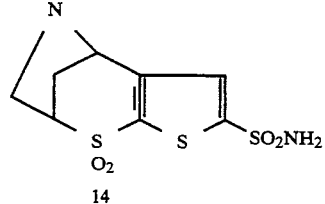
14

Another route to compounds described in this invention involves cyclization of compounds of formula 15 wherein n is 0, 1 or 2 with trialkyl aluminum, preferably trimethyl aluminum in an inert solvent such as toluene, benzene, THF, CHCl₃ or CH₂Cl₃ to yield the cyclic lactam of formula 16.

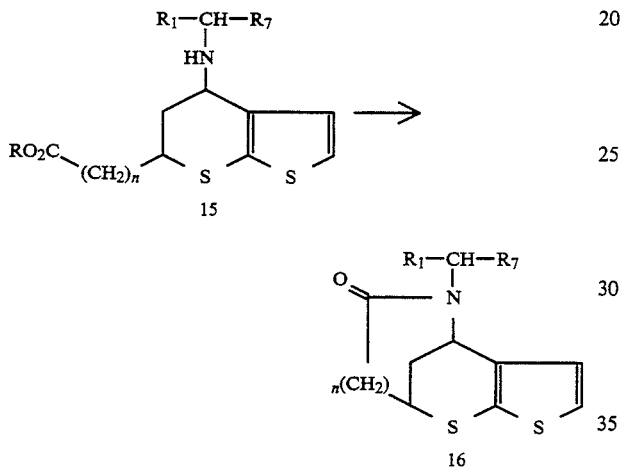

The lactam 16 can be oxidized using normal oxidizing agents such as Oxone®, H₂O₂, m-chloroperbenzoic acid in aqueous alcohol and the like to yield the 1,1-dioxide derivative followed by reduction of the lactam with borane-dimethysulfide in an inert solvent such as, for example, THF, Et₂O, CH₂Cl₂ and the like, to yield the cyclic amine 17. Alternatively, controlled oxidation of lactam 16 with, for instance, NaIO₄, followed by reduction of the lactam moiety yields the corresponding sulfoxide derivative 19.

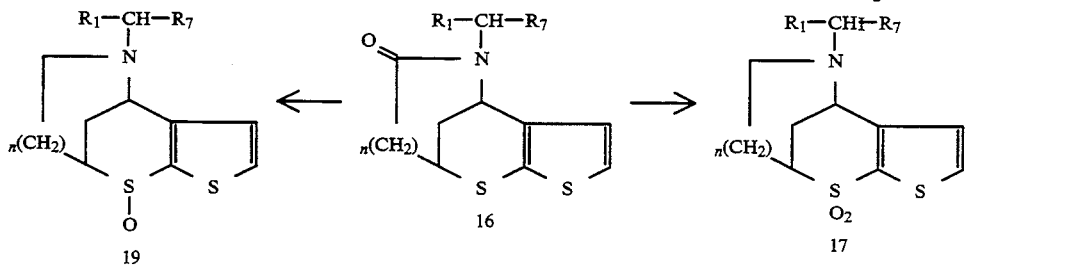

Compounds of formula 18 can be obtained by alkylation of 17 using lithium bis(trialkylsilyl)amides such as lithium bis(trimethylsilyl)amide in an inert solvent such as hexane or THF at temperatures of from about −100° C. to about −50° C. Alkyl halides such as methyl iodide, ethyl iodide, benzyl chloride or sulfonates such as methoxyethoxytrifluoromethane sulfonate and the like can be used as alkylating agents. Subsequently, incorporation of the 2-sulfonamido group is accomplished using methods previously described such as alkyllithium followed by treatment with SO₂ and hydroxylamine-O-sulfonic acid to yield the compound of formula 18. To generate compounds wherein R₁=H, the p-methoxybenzyl protecting groups can be removed in a known fashion using ceric ammonium nitrate or a variety of other reagents. Using essentially the same procedure but substituting either the compound of formula 16 or the compound of formula 19 for that of 17 the corresponding sulfonamides of formulas 20 and 21 are obtained.

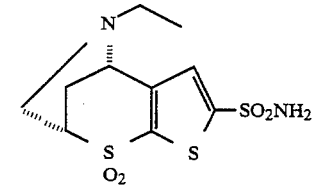
18

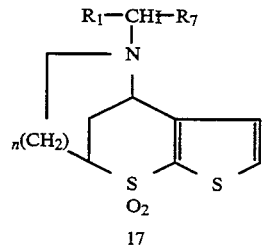
20) m = 0
21) m = 1

As noted previously, the compounds of this invention have a cis-configuration, and each has a pair of enantiomers. The more active enantiomer of each pair is the one in which the nitrogen is joined to the 4-position by a bond shown by convention as a broken line as shown below in structures I and III -continued

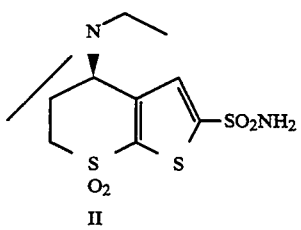

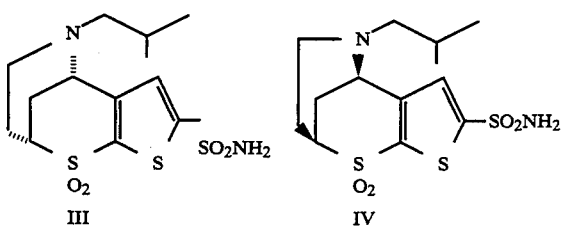

The stereochemical priority rules define the more active cis enantiomer of the one-carbon bridged compounds, I, as (S)(S) and it has an optical rotation of $[\alpha]_D^{25} = -20.97°$.

With a two-carbon bridge, the priority rules define the more active enantiomer III as (S)(R). This more active enantiomer III has an optical rotation of $[\alpha]_D^{25} = +4.8°$. Clearly the sign of the optical rotation in no way defines absolute stereochemistry nor identifies the more active enantiomer of a pair.

The novel pharmaceutical formulations of this invention can be adapted for oral administration such as tablets, capsules or the like; for nasal administration, especially in the form of a spray; for injection, in the form of a sterile injectable liquid; or for topical ocular administration in the form of solutions, suspensions, ointments, solid water soluble polymeric inserts, or gels.

This invention is particularly concerned with formulations adapted for topical ocular administration for the treatment of glaucoma and other stages of elevated intraocular pressure and contain from about 0.1% to about 15% by weight of medicament, especially from about 0.5 to about 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate, a parasympathomimetic agent such as pilocarpine or an ophthalmologically active prostaglandin analog. In such combinations the two active agents are present in approximately pharmacologically equal amounts.

The novel method of treatment of this invention comprises the treatment of elevated intraocular pressure by the administration of a novel compound of this invention or a pharmaceutical formulation thereof. Of primary concern is the treatment by topical ocular administration of from about 0.1 to about 25 mg and especially from about 0.2 to about 10 mg of such compound per day, either by single dose or on a 2 to 4 dose per day regimen.

The following examples illustrate the present invention without, however, limiting the same thereto.

EXAMPLE 1

Preparation of 4-Ethyl-2-[2-(2-methoxyethoxy)ethyl]-2,3,4,5-tetrahydro-2,5-methanothieno[3,2-f]-1,4-thiazepine-7-sulfonamide-1,1-dioxide hydrochloride Step A: Preparation of 5,6-dihydro-7,7-dioxo-4H-thieno[2,3-b]-thiopyran-4-one ethylene-ketal

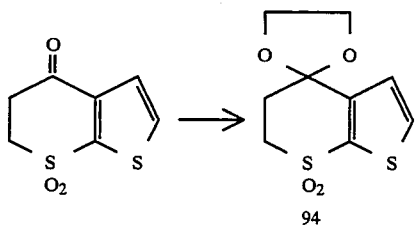

A mixture of 5,6-dihydro-7,7-dioxo-4H-thieno[2,3-b]-thiopyran-4-one (50 g), ethylene glycol (100 mL), p-toluenesulfonic acid (1 g) and toluene (1.5 L) was refluxed under a Dean-Stark apparatus to provide constant removal of water for six hours. To the cooled reaction mixture was added saturated $NaHCO_3$ solution and the layers were separated. The organic phase was extracted twice with $NaHCO_3$ solution (500 mL) and the aqueous layers were back extracted with EtOAc (2×500 ml). The combined organic phases were washed with saturated NaCL solution (3×300 mL) dried over anhydrous sodium sulfate. Filtration and removal of the solvent, followed by recrystallization of the residue from 1-chlorobutane gave 46 g of off-white solid. M.P.=134°–137° C.

Step B: 6-Dimethylaminomethyl-5,6-dihydro-7,7-dioxo-4H-thieno[2,3-b]-thiopyran-4-one, ethylene ketal

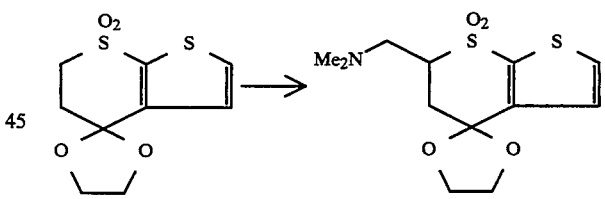

To a stirred solution of 5,6-dihydro-7,7-dioxo-4H-thieno[2,3-b]thiopyran-4-one, ethylene ketal (12 g, 49 mmol) in dry THF (250 ml) under nitrogen at −78° C., was added a solution of lithium bis(trimethylsilyl)amide in hexane (100 ml, 1M, 100 mmol) over 5–10 minutes. After 0.5 hour at −78° C., N,N-dimethylmethyleneammonium iodide (10 g, 54 mmol) was added and the reaction mixture was allowed to warm to 10° C. The reaction mixture was diluted with 10% ammonium chloride solution (500 ml) and extracted with ethyl acetate (3×300 ml). The combined organic extracts were washed with water (2×100 ml), brine (×150 ml) and dried ($Na_2SO_4$). Removal of the filtered, dried solvent gave 10 g of crude solid. Trituration with 1-chlorobutane provided 7.5 g of solid material, used directly in the next step.

Step C: 6-Methylene-5,6-dihydro-7,7-dioxo-4H-thieno[2,3-b]-thiopyran-4one, ethylene ketal

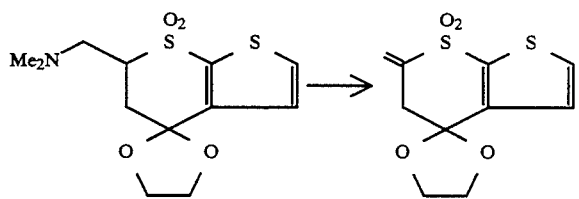

A mixture of the product from Step B (15 g, 49 mmol) and methyl iodide (30 ml) in THF (250 ml) was stirred at ambient temperature for twenty-four hours. The reaction mixture was diluted with ether and filtered. The filtered solid was dissolved in acetonitrile (200 ml) and treated with 1,8-diaza-bicyclo[5.4.0]undec-7-ene (7.5 g, 49 mmol). After stirring for approximately two hours, the solvent was removed under reduced pressure and the residue was partitioned between water and ethyl acetate. The ethyl acetate layer was washed with brine and dried (Na$_2$SO$_4$). Removal of the filtered, dried solvent under reduced pressure gave 9.2 g of solid, used directly in the next step.

Step D: 5,6-Dihydro-7,7-dioxo-6-methyl(thiomethyl)-4H-thieno[2,3-b]-thiopyran-4-one, ethylene ketal

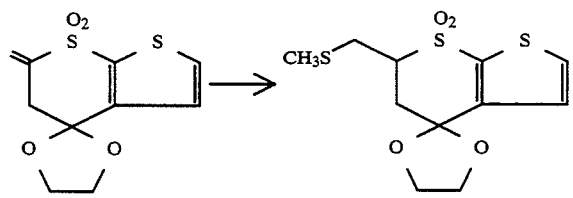

Sodium methanethiolate (2.5 g) was added to a stirred mixture of the product from Step C (9.15 g, 35 mmol) and THF (200 ml). After 0.5 hour, the solvent was removed in vacuo and the residue was partitioned between water and ethyl acetate. The organic layer was washed with water, brine and dried (MgSO$_4$). Removal of the filtered, dried solvent gave 9.5 g of yellowish solid, used directly in the next step.

Step E: 5,6-Dihydro-7,7-dioxo-6-methyl(thiomethyl)-4H-thieno[2,3-b]-thiopyran-4-one

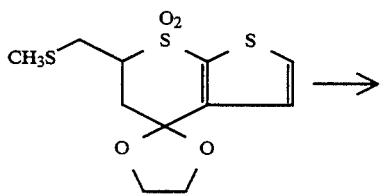

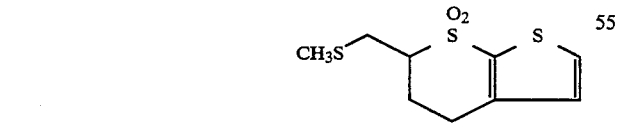

A solution of the product from Step D (9.5 g, 31 mmol) in 6N hydrochloric acid (200 ml) and THF (200 ml) was heated to reflux for about 0.5 hour. The THF was removed under reduced pressure, the residue was filtered and the solid was washed with water until the washings were neutral. The damp solid was used directly in the next step.

Step F: 5,6-Dihydro 4-hydroxy-6-methyl(thiomethyl)-4H-thieno[2,3-b]thiopyran-7,7-dioxide

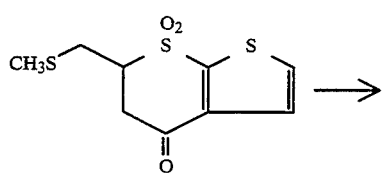

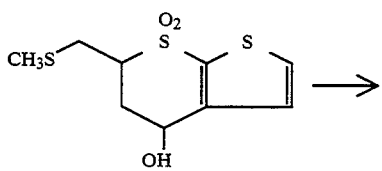

Sodium borohydride (0.60 g, 15.5 mmol) was added to a solution of the product from Step E (8.5 g, 31 mmol) in ethanol (150 ml) and the resulting mixture was stirred for 0.5 hour. After cooling the reaction mixture to 0°–5° C, excess sodium borohydride was destroyed by the addition of 6N hydrochloric acid. The ethanol was removed under reduced pressure, the residue treated with water (150 ml) and extracted with ethyl acetate (3×200 ml). The combined extracts were washed with brine and dried (MgSO$_4$). Evaporation of the filtered, dried solvent gave 7.8 g of an oil, used directly in the next step.

Step G: 5,6-Dihydro-4-methanesulfonyloxy-6-methyl-(thiomethyl)-4H-thieno[2,3-b]thiopyran-7,7-dioxide

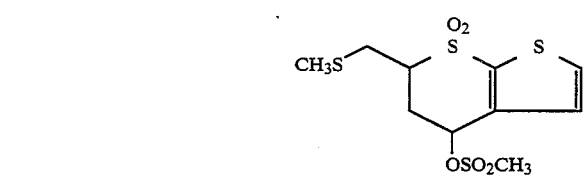

Triethylamine (11.5 ml, 83 mmol) was added to a stirred solution of the product from Step F (7.3 g, 28 mmol) and methanesulfonic anhydride (5.76 g, 33 mmol) in THF (400 ml). After one hour at ambient temperature, the volatiles were removed under reduced pressure. The residue was partitioned between water and ethyl acetate. The ethyl acetate layer was washed with water, brine and dried (MgSO$_4$). Evaporation of the filtered, dried solvent gave 10 g of an oil, used directly in the next step.

Step H: 4-Azido-5,6-dihydro-6-methyl(thiomethyl)-4H-thieno-[2,3-b]thiopyran-7,7-dioxide

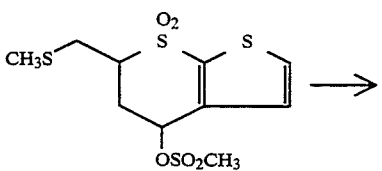

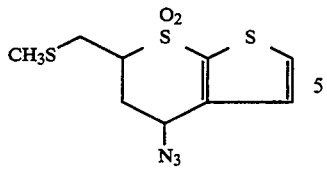

A mixture of sodium azide (2.5 g, 38 mmol) and the product from Step G (10 g, 32 mmol) in DMSO (100 ml) was stirred at ambient temperature for twenty-four hours. The reaction mixture was diluted with water and extracted with ethyl acetate. The organic layer was washed with water, brine and dried ($MgSO_4$). Removal of the filtered, dried solvent under reduced pressure gave 7.8 g of crude solid. Trituration with 1-chlorobutane provided 5.8 g of dried solid used directly in the next step.

Step I: 5,6-Dihydro-4-ethylamino-6-methyl(thiomethyl)-4H-thieno[2,3-b]thiopyran-7,7-dioxide

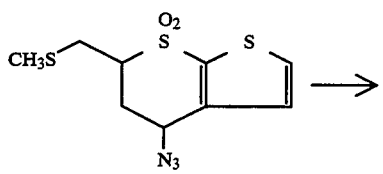

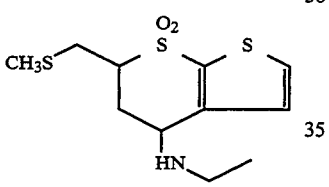

A mixture of triphenylphosphine (2.45 g, 9.4 mmol) and the product from Step H (2.38 g, 7.8 mmol) in THF (25 ml) was stirred at ambient temperature for two hours. Acetaldehyde (7 ml) was added to the reaction mixture and stirring was continued for twenty-four hours. The resulting solution was added to a suspension of sodium borohydride (2.96 g, 78 mmol) in ethanol (300 ml) at 0° C., stirred for 0.5 hour and excess sodium borohydride destroyed by the addition of 6N hydrochloric acid. The residue from removal of the volatiles under reduced pressure was partitioned between water and ethyl acetate. The acidic aqueous phase was neutralized with ammnonium hydroxide and extracted with ethyl acetate. The extracts from the neutralized aqueous phase were washed with brine and dried ($Na_2SO_4$). Removal of the filtered, dried solvent gave 2.7 g of crude product. Ether extraction and evaporation gave 2.1 g of material used directly in the next step.

Step J 4-Ethyl-2,3,4,5-tetrahydro-2,5-methanothieno-[3,2-f]-1,4-thiazepine-1,1-dioxide

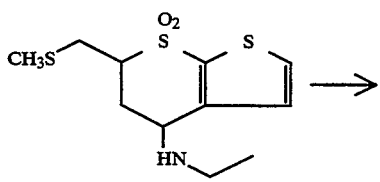

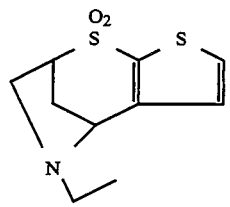

A solution of the product from Step I (3 g, 10 mmol) in 5% aqueous sodium hydroxide (100 ml) and THF (200 ml) was heated to reflux for two hours. The cooled reaction mixture was diluted with brine (100 ml) and extracted with ethyl acetate. The organic extracts were washed with brine and dried ($Na_2SO_4$). Removal of the filtered, dried solvent under reduced pressure gave 2.47 g of an oil that slowly solidified. This material was used directly in the next step.

Step K: 4-Ethyl-2-[2-(2-methoxyethoxy)ethyl]-2,3,4,5-tetrahydro-2,5-methanothieno[3.2-f]-1,4-thiazepine-1,1-dioxide

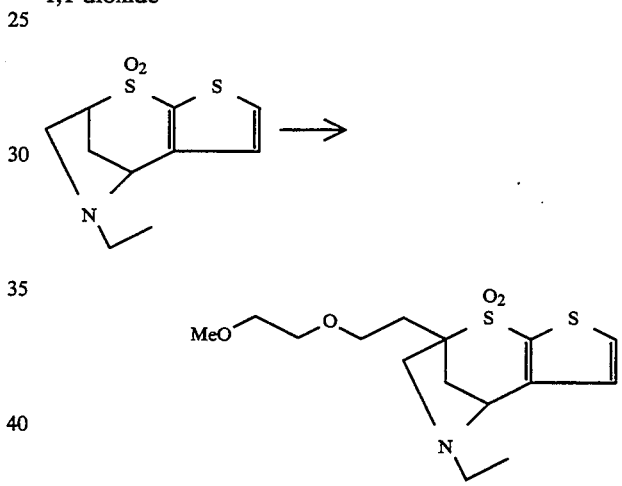

A solution of lithium bis(trimethysilyl)amide in hexane (12.8 ml, 1M, 12.8 mmol) was added to stirred solution of the product from Step J (2.4 g, 9.9 mmol) and 2-(2-methoxyethoxy)ethyl bromide (2.67 ml, 3.6 g, 20 mmol) in THF (50 ml) at −78° C. The reaction mixture was allowed to warm to ambient temperature, diluted with brine and extracted with ethyl acetate. The organic layer was washed with brine and dried ($Na_2SO_4$). Removal of the filtered, dried solvent gave 1.4 g of an oil which was used directly in the next step.

Step L: 4-Ethyl-2-[2-(2-methoxyethoxy)ethyl]-2,3,4,5-tetrahydro-2,5-methanothieno[3,2-f]-1,4-thiazepine-7,7-sulfonamide-1,1-dioxide-hydrochloric

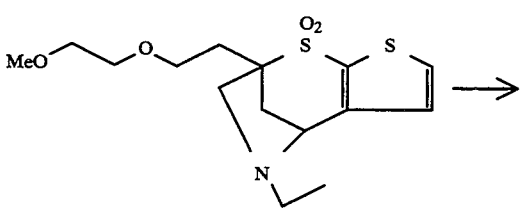

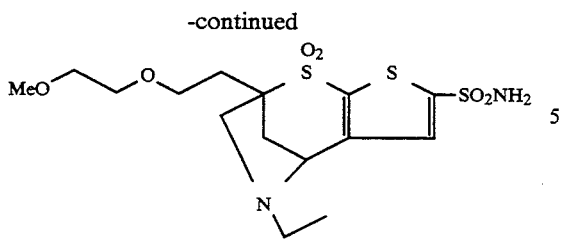

A solution of butyl lithium in hexane (2.7 ml, 2.5M, 6.7 mmol) was added to a solution of the product from Step K (1.15 g, 3.3 mmol) in THF (20 ml) at −78°. After 0.5 hour at this temperature, sulfur dioxide was introduced over the surface of the cold stirred mixture for two minutes. The solvent was removed under reduced pressure, and the residue was dissolved in a solution of sodium acetate hydrate (0.97 g, 10 mmol) in water (20 ml). Hydroxylamine-O-sulfonic acid (1.12 g, 10 mmol) was added and the resulting reaction mixture was stirred for seven hours at ambient temperature. The mixture was adjusted to pH 7.5 by the addition of ammonium hydroxide. After ethyl acetate extraction of the crude product and chromatographic purification (silica gel, CHCl$_3$:CH$_3$OH, 95:5), there was obtained 0.60 g of off-white solid. The material was converted to the hydrochloride salt with ethanolic hydrogen chloride. Trituration of this solid with ether and ethyl acetate gave material of mp 93° C. (foams).

Anal. Calc'd for C$_{15}$H$_{24}$N$_2$O$_6$S$_3$+HCl (461.04): C, 39.08; H, 5.47; N, 6.08. Found: C, 39.18; H, 5.71; N, 5.80.

EXAMPLE 2

Preparation of
5-(4-Methoxybenzyl)-2-methyl-3,4,5,6-tetrahydro-2H-2,6-methanothieno[3,2-g]-1,5-thiazocine-8-sulfonamide-1,1-dioxide

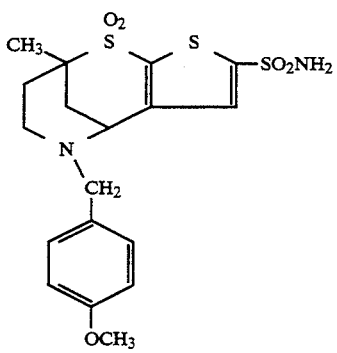

Step A: Preparation of 3-(2-thienylthio) glutaric acid

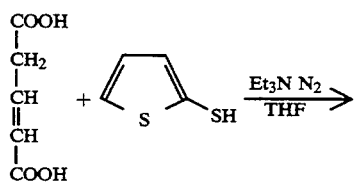

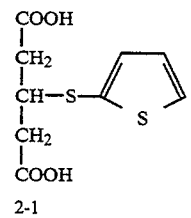

To a stirred solution of glutaconic acid (50.0 g, 0.43 mol) in dry tetrahydrofuran (500 ml) under nitrogen was added triethylamine (130 ml, 0.90 mol) followed by 2-thiophenethiol (50.0 g, 0.43 mol). The mixture was stirred at room temperature over the weekend. The mixture was concentrated in vacuo and the residual oil was poured into cold 6N HCl (600 ml). This was extracted with ethyl acetate (200 and 4×100 ml). The combined extracts were washed free of strong acid using saturated sodium chloride, dried, filtered and concentrated in vacuo. The product, 2-1, was a beige solid (103.4 g), m.p. 119°–123° C. Yield was 98%.

Step B: Preparation of 5,6-dihydro-4H-4-oxothieno-[2,3-b]thiopyran-6-acetic acid hydrochloride

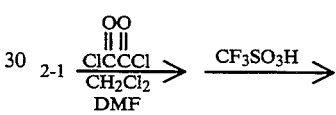

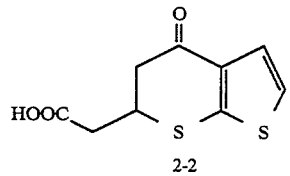

To a stirred suspension of 3-(3-thienylthio)glutaric acid (103.4 g, 0.42 mmol) in dry methylene chloride (400 ml) was added dimethylformamide (3 ml) followed by the dropwise addition of oxalyl chloride (87 ml, 1.0 mol) added over 1¼ hours. The resulting solution was stirred for 2½ hours at room temperature and then was concentrated in vacuo. The residual oil was taken up in dry methylene chloride (350 ml) and the solution was cooled to −78° C. Trifluoromethanesulfonic acid (74.3 ml, 0.84 mol) was added dropwise over ½ hour and stirring was continued for ¼ hour at −78° C. Then the temperature was allowed to rise to 15° C. over 1¼ hours and the mixture was poured into ice and water (1500 ml). This mixture was stirred overnight under nitrogen in an open beaker. The semi-solid which had formed was separated by decanting the aqueous solution. The solid remaining was stirred in ether (800 ml) and a tan solid formed. The solid was dissolved in ethyl acetate and the combined ether-ethyl acetate solutions were washed free of strong acid with saturated sodium chloride, dried, filtered and concentrated in vacuo. The product 2—2 was a tan solid (93.8 g), mp 112°–117° C. Yield was 98%.

Step C: Preparation of Ethyl 5,6-dihydro-4-oxo-4H-thieno[2,3-b]thiopyran-6-acetate

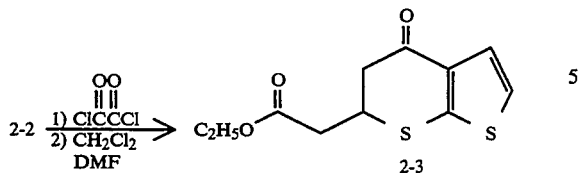

5,6-Dihydro-4-oxo-4H-thieno[2,3-b]thiopyran-6-acetic acid (78.0 g, 0.34 mol) was stirred in dry methylene chloride (450 ml) containing dimethylformamide (¼ ml) and oxalyl chloride (45 ml, 0.51 mol) was added dropwise over 20 minutes. The mixture was stirred at room temperature for 3 hours and then was concentrated in vacuo. The residual oil was taken up in ice cold ethanol (200 ml). The solution was stirred at room temperature for 2 hours and was concentrated in vacuo. The residual oil was taken up in ethyl acetate and was washed with saturated sodium bicarbonate, saturated sodium chloride and was dried, filtered and concentrated in vacuo to give 72.2 g, of the liquid ester. Crude yield was 83%.

Step D: Preparation of Ethyl 5,6-dihydro-4-hydroxy-4H-thieno-[2,3-b]thiopyran-6-acetate

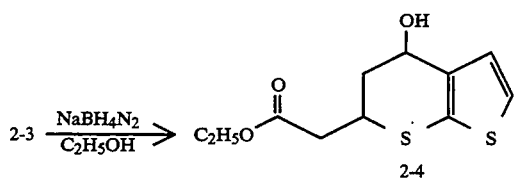

To a stirred solution of ethyl 5,6-dihydro-4-oxo-4H-thieno[2,3-b]thiopyran-6-acetate (72.2g, 0.28 mol) in ethanol (300 ml) under nitrogen and cooled to 0° C. was added sodium borohydride (2.65 g, 0.07 mol). The mixture was stirred for 1½ hours at 0° C. and then additional sodium borohydride (1.32 g, 0.035 mol) was added. Stirring was continued for 2 hours at room temperature. Acetone (25 ml) was added and the mixture was concentrated in vacuo. The residual oil was purified by chromatography on silica gel (300 g) using 70:30 hexane:ethyl acetate. The alcohol was recovered as a yellow solid (48 g). Yield was 66%.

Step E: Preparation of cis Ethyl 5,6-Dihydro-4-(4-methoxybenzyl-amino)-4H-thieno[2,3-b]thiopyran-2-ylacetate

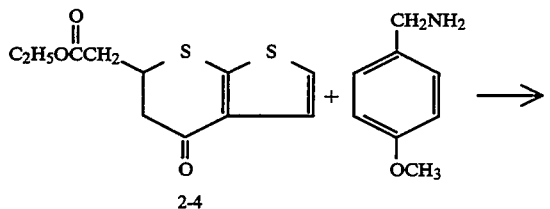

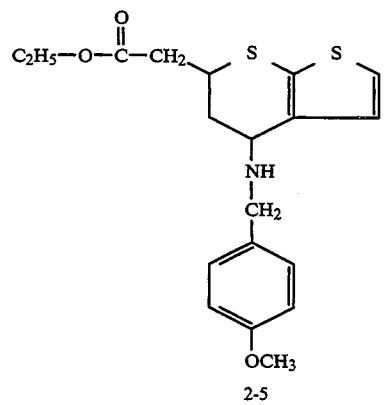

To a solution of ethyl 5,6-dihydro-4-oxo-4H-thieno[2,3-b]-thiopyran-6-ylacetate (10 g, 39 mmol) in THF (110 ml) and toluene (110 ml) at 0° C. was added 4-methoxybenzylamine (25.5 ml, 26.8 g, 195 mmol). Titanium tetrachloride (2.2 ml, 3.8 g, 20 mmol) was added to the cold solution and the resulting mixture was stirred for 0.75-1 hour. The mixture was added to a cold (0° C.) stirred suspension of sodium borohydride (4.5 g, 120 mmol) in EtOH (900 ml). The resulting mixture was stirred for about 1 hour and acidified to pH 1 with 3N hydrochloric acid. The solvent was removed in vacuo and the residue partitioned between ethyl acetate and sodium bicarbonate solution. The ethyl acetate layer was separated, dried over anhydrous sodium sulfate and evaporated to give a mixture of cis and trans isomers of the title compound. Flash chromatography on silica gel eluting with ethyl acetate/hexane (1:4) gave 9.7 g of cis isomer after solvent removal and drying.

Step F: Preparation of 5-(4-Methoxybenzyl)-4-oxo-3,4,5,6-tetrahydro-2H-2,6-methano[3,2-g]-1,5-thiazocine-1,1-dioxide

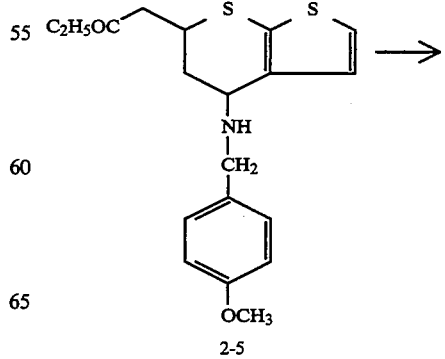

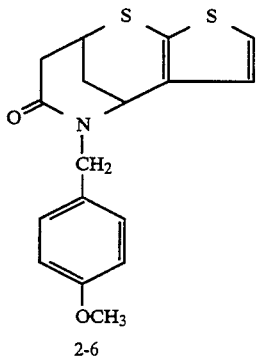

2-6

A solution of (CH$_3$)$_3$Al in toluene (23 ml, 2M, 46 mmol) was added to a stirred solution of the product from Step E (8.7 g, 23 mmol) in toluene (575 ml) at 0° C. The reaction mixture was brought to ambient temperature and then heated to reflux for four hours. The reaction mixture was cooled in an ice bath and treated with 3N hydrochloric acid (100 ml) and diluted with H$_2$O (500 ml) and ethyl acetate (500 ml). The layers were separated and the organic phase was washed with H$_2$O, brine and dried over anhydrous sodium sulfate. Removal of the filtered, dried solvent under reduced pressure gave 6.6 g of crude product. Recrystallization from hexane/ethyl-acetate gave material of mp 123°-125° C.

Anal. Calc'd for C$_{17}$H$_{17}$NO$_2$S$_2$ (331.47): C, 61.60; H, 5.18; N, 4.23. Found: C, 61.75; H, 5.15; N, 4.42.

Step G: Preparation of 5-(4-Methoxybenzyl)-4-oxo-3,4,5,6-tetrahydro-2H-2,6-methano[3,2-g]-1,5-thiazocine-1,1-dioxide

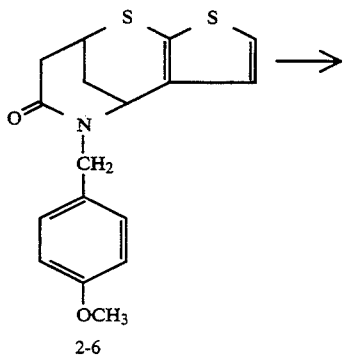

2-6

A solution of Oxone® (0.83g, 1.35 mmol) in H$_2$O (12.4 ml) was added to a stirred solution of the product from Step F (0.15 g, 45 mmol) in CH$_3$OH (6.2 ml). After stirring for two hours, the reaction mixture was extracted with ethyl acetate. The organic layer was washed with 10% aqueous sodium bisulfite solution, brine and dried over anhydrous sodium sulfate. Removal of the filtered, dried solvent gave 0.14 g of crude product. Two recrystallizations from hexane/ethyl acetate provided material of mp 196°-198° C.

Anal. Calc'd for C$_{17}$H$_{17}$NO$_4$S$_2$ (363.47): C, 56.17; H, 4.72; N, 3.85. Found: C, 56.24; H, 4.68; N, 3.85.

Step H: Preparation of 5-(4-Methoxybenzyl)-3,4,5,6-tetrahydro-2-H-2,6-methano[3,2-g]-1,5-thiaocine-1,1-dioxide

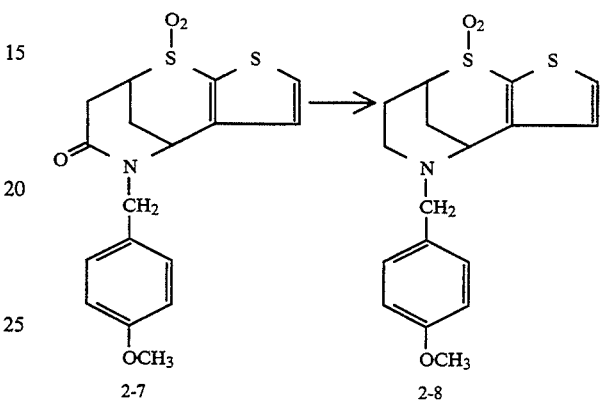

2-7        2-8

A solution of the product from Step G (1.0 g, 2.8 mmol) and borane dimethylsulfide (0.84 ml, 10M in THF, 8.4 mmol) in THF (11 ml) was heated under reflux for two hours. The solvent was removed and the residue was heated with 6N hydrochloric acid (8.5 ml) for 20 minutes to destroy the amine borane complex. The cooled mixture was neutralized with aqueous sodium bicarbonate solution and extracted with ethyl acetate. The organic extract was dried over anhydrous sodium sulfate, filtered and evaporated under reduced pressure to give an off-white foam. Flash chromatography over silica gel eluting with 40% ethyl acetate/60% hexane provided material of mp 167°-168° C.

Anal. Calc'd for C$_{17}$H$_{19}$NO$_3$S$_2$ (349.49): C, 58.42; H, 5.49; N, 4.01. Found: C, 58.42; H, 5.53; N, 4.04.

Step I: Preparation of 5-(4-Methoxybenzyl)-2-methyl-3,4,5,6-tetrahydro-2H-2,6-methanothieno[3,2-g]-1,5-thiazocine-1,1-dioxide

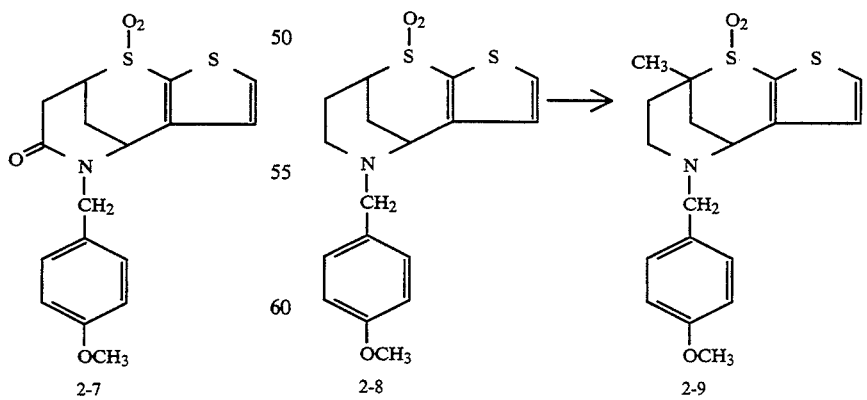

2-7        2-8        2-9

A solution of lithium bis(trimethylsilyl)amide in hexanes (28 ml, 1M, 28 mmol) was added dropwise to a stirred solution of the product from Step H (8.0 g, 23 mmol) in THF (200 ml) at −78° C. When addition was complete, methyl iodide (6.5 g, 46 mmol) was added at this temperature, then the reaction mixture was allowed to warm to ambient temperature and stirred overnight. The solvent was removed under reduced pressure and the residue was taken up in $H_2O$ (300 ml) and extracted with ethyl acetate (3×300 ml). The combined organic extracts were washed with brine and dried over anhydrous sodium sulfate. Removal of the filtered, dried solvent under reduced pressure, followed by flash chromatography (silica gel, 30% ethyl acetate/70% hexane) of the residue (8.4 g) gave 6.5 g of white solid, used directly in the next step.

$^1$H-NMR: ($CDCl_3$) δ1.81(3H, S, 2-$CH_3$); 3.81 (3H, S, —$OCH_3$).

Step J: Preparation of 5-(4-Methoxybenzyl)-2-methyl-3,4,5,6-tetrahydro-2H-2,6-methanothieno[3,2-g]-1,5-thiazocine-8-sulfonamide-1,1-dioxide

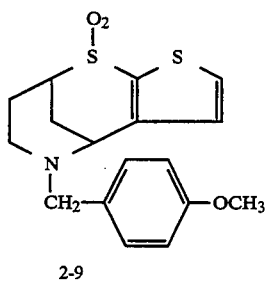

2-9

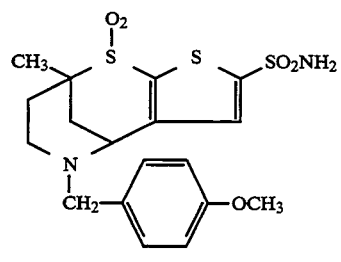

2-10

A solution of butyl lithium in hexane (8.0 ml, 2.5M, 20 mmol) was added to a stirred solution of the product from Step I (6.3 g, 17 mmol) in THF (145 ml) at −78° C. After stirring at this temperature for two hours, sulfur dioxide was introduced over the surface of the stirred reaction mixture for twenty minutes. The reaction mixture was stirred an additional 0.25 hour at this temperature and allowed to warm to ambient temperature. The solvent was removed under reduced pressure and the residue was dissolved in a solution of sodium acetate trihydrate (6.5 g, 48 mmol) in water (62 ml) at 0° C. Hydroxylamine-O-sulfonic acid (4.6 g, 41 mmol) was added and the mixture was stirred overnight at ambient temperature. The mixture was treated with a solution of saturated sodium bicarbonate solution (50 ml), diluted with water (1500 ml) and extracted with ethyl acetate. The organic extracts were washed with brine and dried over anhydrous sodium sulfate. Removal of the filtered, dried solvent under reduced pressure followed by trituration of the residue with ethyl acetate and methanol gave 4.0 g of white solid. An additional 1.4 g was obtained from flash chromatography (silica gel, 40% ethyl acetate, 60% hexane) of the material obtained by evaporation of the trituration solvents. Recrystallization from methanol-ethyl acetate-hexane gave material of mp 254°–256° C.

Anal. Calc'd for $C_{18}H_{22}N_2O_5S_3$ (442.60): C, 48.84; H, 5.02; N, 6.33. Found: C, 48.85; H, 5.06; N, 6.06.

EXAMPLE 3

Preparation of 5-(4-Methoxybenzyl)-2-methoxypropyl-3,4,5,6-tetrahydro-2H-2,6-methanothieno[3,2-g]-1,5-thiazocine-8-sulfonamide-1,1-dioxide The title compound, mp 190°–193° C, was prepared following the procedure of steps A-J of Example 2, but substituting methoxypropyl iodide for methyl iodide in Step I.

EXAMPLE 4

Preparation of 2-Methyl-3,4,5,6-tetrahydro-2H-2,6-methanothieno[3,2g]-1,5-thiazocine-8-sulfonamide-1,1-dioxide hydrochloride

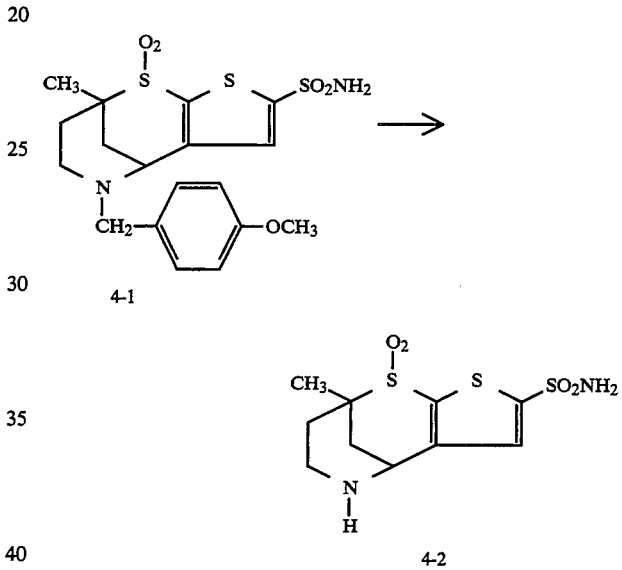

4-1

4-2

A solution of ceric ammonium nitrate (32.9 g, 60 mmol) in water (76 ml) was added to a solution of 5-(4-methoxybenzyl)-2-methyl-3,4,5,6-tetrahydro-2H-2,6-methanothieno[3,2-g]-1,5-thiazocine-8-sulfonamide-1,1-dioxide (5.2 g, 12 mmol) in acetonitrile (790 ml). After stirring for 24 hours at ambient temperature, the acetonitrile was removed under reduced pressure. The resulting mixture was diluted with water, made alkaline by the addition of aqueous ammonia and extracted with ethyl acetate. The ethyl acetate layer was washed with brine and dried over anhydrous sodium sulfate. The residue obtained from evaporation of the filtered, dried solvent was chromatographed (silica gel, $CHCl_3$/MeOH/$NH_4OH$, 90:10:1) to give 1.9 g of off-white solid. Treatment with methanolic hydrogen chloride, followed by recrystallization from methanol gave material of mp>290° C.

Anal. Calc'd for $C_{10}H_{14}N_2O_4S_3$+HCl (358.90): C, 33.46; H, 4.22; N, 7.81. Found: C, 33.31; H, 3.87; N, 7.57.

EXAMPLE 5

Preparation of 2-Methoxypropyl-3,4,5,6-tetrahydro-2H-2,6-methanothieno[3,2-g]-1,5-thiazocine The title compound, mp 265°–267° C, was prepared following the procedure of steps A to F and H and I of Example 2, but substituting methoxypropyl iodide for methyl iodide in Step I, and then following the procedure of Example 4.

EXAMPLE 6

5-Isobutyl-4-oxo-3,4,5,6-tetrahydro-2H-2,6-methanothieno[3,2-g]- 1,5-thiazocine-8-sulfonamide

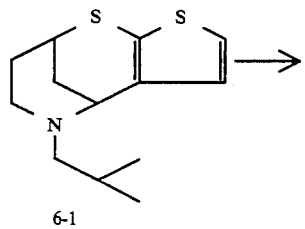

6-1

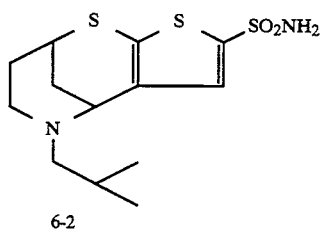

6-2

5-Isobutyl-4-oxo-3,4,5,6-tetrahydro-2H-2,6-methanothieno[3,2-g]-1,5-thiazocine, prepared as described in Example 1, steps A, B and C but substituting isobutylamine for 4-methoxybenzylamine (4 g, 15 mmol), was added to a mixture of phosphorous pentachloride (6.23 g, 30 mmol) and chlorosulfonic acid (7 ml) at 0° C. After 0.5 hour at this temperature and 0.5 hour at 50° C., the reaction mixture was poured over crushed ice. The resulting sulfonyl chloride was separated and treated with concentrated aqueous ammonia (100 ml) in ethyl acetate (100 ml) at 0° C. The ethyl acetate layer was separated and evaporated under reduced pressure. The resulting solid was chromatographed over silica gel (ethyl acetate: hexane; 1:1) to give 2.0 g of the title compound.

EXAMPLE 7

5-Isobutyl-4-oxo-3,4,5,6-tetrahydro-2H-2,6-methanothieno[3,2-g]-1,5-thiazocine-8-sulfonamide-1,1-dioxide

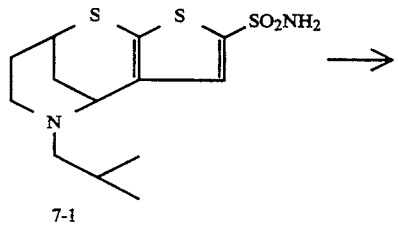

7-1

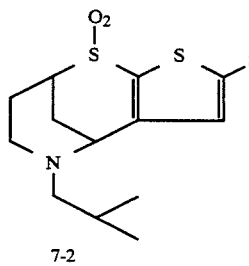

7-2

5-Isobutyl-4-oxo-3,4,5,6-tetrahydro-2H-2,6-methanothieno[3,2-g]-1,5-thiazocine-8-sulfonamide (2 g, 5.8 mmol) was added to a mixture of Oxone® (10 g, 16.3 mmol) and methanol (25 ml). After 24 hours, the reaction mixture was diluted with water (50 ml) and extracted with ethyl acetate (3×50 ml). After drying over sodium sulfate, the solvent was evaporated under reduced pressure to yield 2.13 of a foam. A sample triturated with 1-chlorobutane gave material with mp 239°–241° C.

Anal. Calc'd for $C_{13}H_{18}N_2O_5S_3$ (378.50): C, 41.25; H, 4.80; N, 7.40. Found: C, 41.48; H, 4.78; N, 7.24.

EXAMPLE 8

5-Isobutyl-3,4,5,6-tetrahydro-2H-2,6-methanothieno-[3,2-g]-1,5-thiazocine-8-sulfonamide-1,1-dioxide-hydrochloride

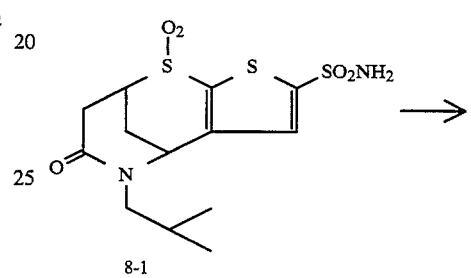

8-1

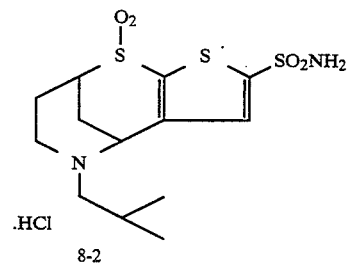

8-2

A solution of borane dimethyl sulfide in THF (5.5 ml, 10M, 55 mmol) was added to a solution of 5-isobutyl-4-oxo-3,4,5,6-tetrahydro-2H-2,6-methanothieno[3,2-g]-1,5-thiazocine-8-sulfonamide-1,1-dioxide(2.1 g, 5.5 mmol) in THF (25 ml) and heated at reflux for two hours. Dilute hydrochloric acid (25 ml,3N) was added and refluxing was continued for an additional two hours. The THF was removed under reduced pressure, the residue was diluted with water (50 ml), saturated sodium bicarbonate solution (50 ml) and extracted with ethyl acetate (3×50 ml). The ethyl acetate extracts were washed with brine, dried (Na₂SO₄) and evaporated to give 1 g of off-white solid. The material was converted to the hydrochloride salt with ethanolic hydrogen chloride, mp 264°–265° C.

Anal. Calc'd for $C_{13}H_{20}N_2O_4S_3$+HCl (401.02): C, 38.93; H, 5.29; N, 6.99. Found: C, 38.99; H, 5.29; N, 6.89.

(−) 5-Isobutyl-3,4,5,6-tetrahydro-2H-2,6-methanothieno[3,2-g]-1,5-thiazocine-8-sulfonamide 1,1-dioxide hydrochloride and (+) 5-Isobutyl-3,4,5,6-tetrahydro-2H-2,6-methanothieno[3,2-g]-1,5-thiazoncine-8-sulfonamide 1,1-dioxide hydrochloride.

(+) 5-Isobutyl-3,4,5,6-tetrahydro-2H-2,6-methanothieno[3,2-g]-1,5-thiazocine-8-sulfonamide-1,1-dioxide (0.590 g, 1.62 mmol) and di-p-toluoyl-L-tartaric acid (0.164 g, 0.424 mmol) were dissolved in a minimum amount of hot ethanol. The solution was cooled to 20° C. and the crystals which formed on standing were collected by filtration. The filtrate was saved. The collected solid was recrystallized two additional times from ethanol. The salt was treated with saturated sodium bicarbonate and ethyl acetate, and the ethyl acetate washed with saturated sodium chloride. The organic phase was dried over magnesium sulfate, filtered, and the solvent removed in vacuo. The remaining solid was treated with methanolic hydrogen chloride, and the volatiles removed in vacuo. The residue was dissolved in methanol and the volatiles removed in vacuo (repeated two times). The (−) isomer of the title compound was obtained as a white solid (60 mg). $[\alpha]_D^{20}$ −6.3 (c=0.7, methanol). Analysis Calculated for $C_{13}H_{20}N_2O_4S_3 \cdot HCl$ C, 38.98; H, 5.29; N, 6.99. Found. C, 39.02; H, 5.42; N, 6.65. The filtrate which was saved was reduced to dryness in vacuo and the residue partitioned between ethyl acetate and saturated sodium bicarbonate. The ethyl acetate was washed with saturated sodium chloride solution, then dried over magnesium sulfate. Filtration and evaporation gave a solid (0.450 g, 1.23 mmol) which was dissolved in a minimum amount of ethanol along with di-p-toluoyl-D-tartaric acid (0.236 g, 0.611 mmol). The crystals which formed were collected and recrystallized twice more from ethanol. The compound thus obtained was converted to the hydrochloride salt as described above, to give the (+) isomer of the title compound $[\alpha]_D^{20}$ +4.8 (C=0.5, methanol). Analysis. Calculated for $C_{13}H_{20}N_2O_4S_3 \cdot HCl \cdot \frac{1}{2}H_2O$: C, 38.08; H, 5.41; N, 6.83. Found: C, 38.28; H, 5.22; N, 6.72.

EXAMPLE 9

5-Propyl-3,4,5,6-tetrahydro-2H-2,6-methanothieno[3,2-g]-1,5-thiazocine-8-sulfonamide-1,1-dioxide hydrochloride The title compound, mp 282°–283° C. (dec), was prepared following the procedures of examples 6–8 except using as starting material in example 6, 5-propyl-4-oxo-3,4,5,6-tetrahydro-2H-2,6-methanothieno-[3,2-g]-1,5-thiazocine, which was prepared as described in Steps A,B and C of Example 1 substituting propylamine for 4-methoxybenzylamine.

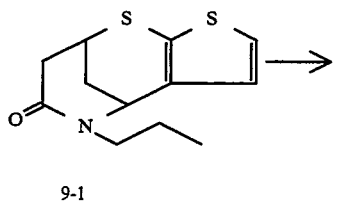

9-1

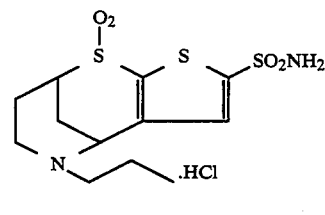

9-2

Anal. Calc'd for $C_{12}H_{18}N_2O_4S_3$ +HCl (386.94): C, 37.24; H, 4.68; N, 7.23. Found: C, 36.92; H, 4.80; N, 7.20.

EXAMPLE 10

2,5-Methanothieno[3,2-f]-1,4-thiazepine-7-sulfonamide-4-propyl-2,3,4,5-tetrahydro-1,1-dioxide.•HCl

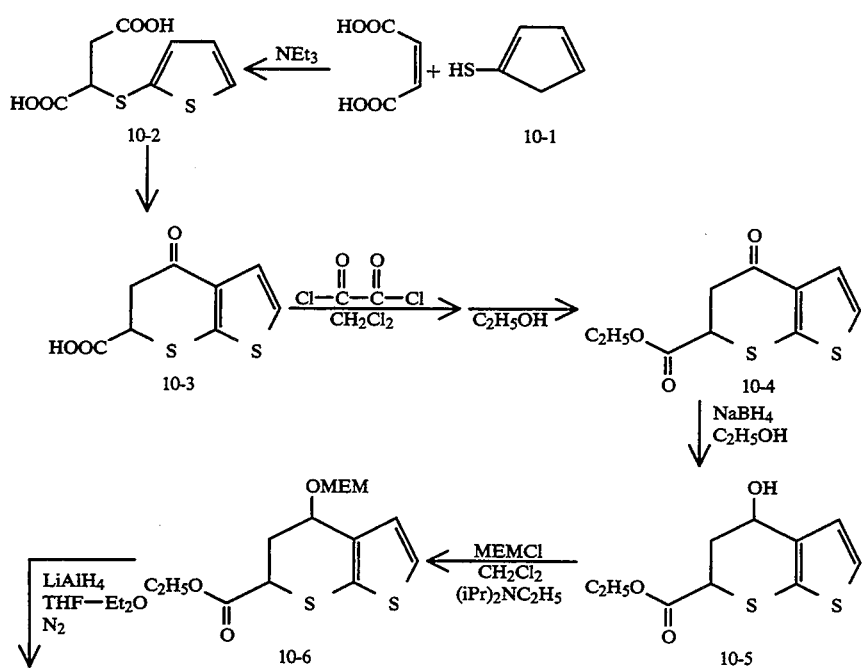

-continued

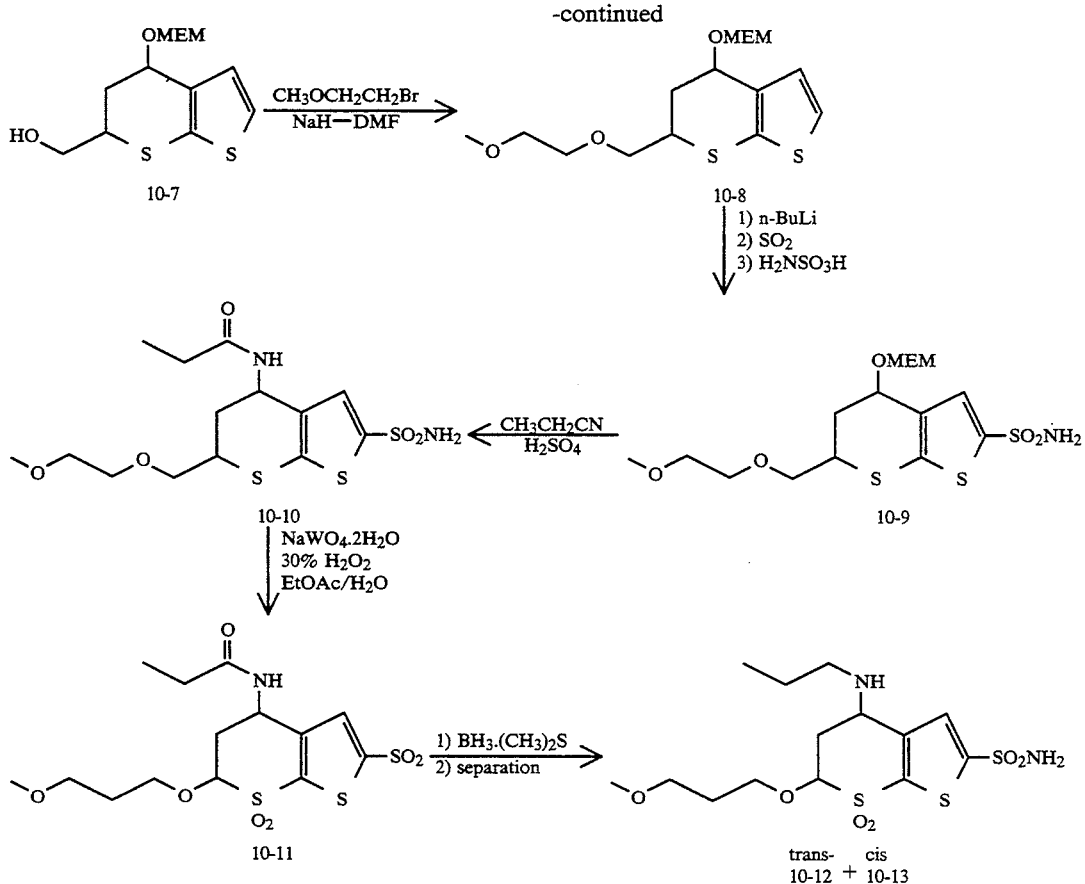

Step A: Preparation of 2-(2-thienylthio)succinic acid (2)

To a stirred solution of maleic acid (6.38 g, 0.055 mmol) in tetrahydrofuran (50 ml) under a nitrogen atmosphere was added 2-thiophenethiol (1)(5.0 ml, 0.055 mol) and triethylamine (14.2 g, 0.14 mol). The mixture was stirred at gentle reflux for 16 hours overnight. The solvent was removed in vacuo and the residual oil was poured into 3N HCl (200 ml). The product was extracted into ethyl acetate (125 ml) in three portions, washed with saturated NaCl solution and dried over $Na_2SO_4$. The solution was filtered and concentrated in vacuo to give 11.9 g of 2 (93%) as a light beige solid, 136°–138.5° C. of 95% purity by HPLC. This reaction was scaled up to 1.0 mole with no change in the results.

Step B: Preparation of 5,6-dihydro-4-oxo-4H-thieno[2,3-b]thiophene-6-carboxylic acid(3)

To a stirred suspension of 2 (75.5 g, 0.325 mol) in methylene chloride (500 ml) under a nitrogen atmosphere was added dimethylformamide (3 ml) followed by the dropwise addition of oxalyl chloride (70.7 ml, 0.81 mol) over a ½ hour period. The mixture was stirred at ambient temperature for 2-½ hours and the resulting solution was concentrated in vacuo to a brown oil. Then ½ of this oil was dissolved in methylene chloride (200 ml), cooled to about −78° C. and stirred as trifluoromethanesulfonic acid (50 g, 0.33 mol) was added dropwise over 5 minutes. After ¼ hour at −78° C., the cooling bath was removed and the temperature was allowed to rise to room temperature. After 4-¾ hours, the mixture was poured into ice and water. Methylene chloride (400 ml) was added and filtered to obtain 3 as a pale gray solid (4.1 g). The methylene chloride layer was separated washed with $H_2O$, dried over $NaSO_4$, filtered and concentrated in vacuo to a black gum. The gum was dissolved in ethyl acetate (150 ml). The solution was extracted with 10×50 ml of 0.25N KOH. The individual extracts were acidified and the solids were filtered and dried to yield 19 g (55%) of 3, m.p. 182.5°–184° C.

Step C: Ethyl 5,6-dihydro-4-oxo-4H-theino[2,3-b]thiopyran-6-carboxylate (4)

Compound 3 (21.4 g, 0.10 mol) was suspended in methylene chloride (200 ml) containing dimethyl formamide (15 drops) and oxalyl chloride (12.2 ml, 0.14 mol) was added dropwise with stirring over ¼ hour at room temperature, stirred for an additional ¾ hour and then concentrated in vacuo. A dark gray solid resulted. The solid was taken up in dry methylene chloride (50 ml) and ethanol 100 ml) was added with cooling: stirred at ambient temperature overnight. The reaction solution was concentrated in vacuo and the dark oil was extracted into ethyl acetate (100 ml). The organic extracts were washed with water, saturated sodium bicarbonate, again with water, dried, filtered and concentrated in vacuo to yield 4, 22.3 g (92%) as viscous liquid. Upon refrigeration, the liquid solidified to a brown waxy solid.

Step D: Preparation of Ethyl 5,6-dihydro-4-hydroxy-4H-thieno[2,3-b]thiopyran-6-carboxylate (5)

Compound 4 (21.6 g, 0.089 mol) was dissolved in ethanol (100 ml) under nitrogen. The solution was cooled in ice and sodium borohydride (1.0 g, 0.026 mol) was added. The mixture was stirred at ambient temperature for 3 hours. Then additional sodium borohydride (0.5 g, 0.013 mol) was added and stirring was continued for ¾ hour. Acetone (10 ml) was added and the mixture was concentrated in vacuo. The residual oil was taken up in ethyl acetate (150 ml) and water (100 ml). The organic layer was separated and washed with saturated sodium bicarbonate, water, dried, filtered and concentrated in vacuo to yield 18.3 g of 5 (84%).

Step E: Preparation of Ethyl 5,6-dihydro-4-methoxyethoxymethoxy-4H-thieno[2,3-b]thiopyran-6-carboxylate (6)

Compound 5 (18.3 g, 0.075 mol) was dissolved in dry methylene chloride (100 ml) and the solution was cooled in ice. Diisopropylethylamine (10.7 g, 0.083 mol) was added followed by MEM chloride (10.3 g, 0.083 ml). The mixture was stirred for 72 hrs. at room temperature. The reaction was then poured into ice and water (300 ml). The methylene chloride layer was separated, washed with 2N hydrochloric acid, saturated sodium bicarbonate, water, dried filtered and concentrated in vacuo to yield the MEM ether 6 (23.5 g) as a liquid in 94% yield.

Step F: Preparation of 5,6-dihydro-6-hydroxymethyl-4-methoxyethoxymethoxy-4H-thieno[2,3-b]thiopyran (7)

Compound 6 (23.5 g, 0.07 tool) was dissolved in tetrahydrofuran (50 ml). The solution was added dropwise under nitrogen to a stirred suspension of lithium aluminum hydride (3.3 g, 0.0875 mol) in anhydrous ether (100 ml) with cooling in ice. The mixture was stirred at ambient temperature for 15 hrs. The reaction was then cooled in ice and decomposed by carefully adding dropwise water (3.5 ml), 20% sodium hydroxide (2.6 ml) and water (12.3 ml). The mixture was diluted with ether (100 ml) and filtered. The solids were washed with ether. The combined ether solutions were washed with saturated sodium chloride, dried, filtered and concentrated in vacuo to yield 20.3 g 7 (50%) as a pale yellow oil.

Step G: Preparation 5,6-dihydro-6-(2-methoxyethoxymethyl)4-methoxyethoxymethoxy-4H-thieno[2,3-b]thiopyran (8)

Under N$_2$, a suspension of 60% NaH (20 g, 0.5 mol), DMF (350 ml) and 7 (38.3 g, 0.13 mol) was stirred at ambient temperature. After 2.5 h. the reaction was cooled to 0°-4° C. and 2-methoxyethylbromide (71 g, 0.51 mol) was added dropwise. After complete addition, the reaction was allowed to stir to room temperature overnight. The solution was then poured into H$_2$O and the aqueous layer was extracted with EtOAc (3x). The organic layer was washed with saturated NaCl, dried, filtered and concentrated to dryness. The residue was chromatographed on a Still column with silica gel and the product eluted with 20% EtOAc-hexane to yield 39 g (84%) of 8.

Step H: Preparation of 5,6-dihydro-6-(2-methoxyethoxymethyl)-4-(2-methoxyethoxymethoxy)-4H-thieno[2,3-b]thiopyran (9)

To a solution of 8 (39 g, 0.11 mol) in THF (300 ml) under N$_2$ cooled to −78° C. was added dropwise a solution of n-BuLi in hexane (2.5M, 60 ml, 0.15 ml). After addition, SO$_2$ gas was passed over the surface for 20 min. the solution was stirred at −78° C. for 1 h., and then at room temperature for 2 h. The reaction was concentrated to dryness and the residue was treated with H$_2$O (300 ml), NaOAc•3H$_2$O (47.1 g, 0.36 mol) and hydroxylamine O-sulfonic acid (32.4 g, 0.29 mol). After stirring overnight at room temperature, the pH of the solution was adjusted to 8.5 and extracted with EtOAc (3×). The organic extracts were dried, filtered and concentrated to dryness to yield 45.2 g (93%) of 9.

Step I: Preparation of 5,6-dihydro-6-(2-methoxyethoxymethyl)-4-propionamido-4H-thieno[2,3-b]thiopyran-2-sulfonamide 10

To a cold mixture (−10° C.) of 9 (45.2 g, 0.11 mol) in propionitrile (500 ml) under N$_2$ was added dropwise concentrated sulfuric acid (38 ml, 0.71 mol). After 1 h, the solution was allowed to stir at r.t. for 2 h and then poured onto ice. The cold aqueous was extracted with EtOAc (3×), and the organic extracts were washed with saturated NaCl, dried, filtered and concentrated to dryness to yield 37.3 g (89%)of 10.

Step J: Preparation of 5,6-dihydro-6-(2-methoxyethoxymethyl)-4-propionamido-4H-thieno[2,3-b]thiopyran-2-sulfonamide-7,7-dioxide (11)

To a solution of 10 (37.3 g, 0.095 mol) in EtOAc (1 l) under N$_2$ stirred at r.t. was added NaWO$_4$•2H$_2$O (2.9 g, 0.009 mol) in H$_2$O (45 mol). After 15 min., 30% H$_2$O$_2$ (27 ml, 0.26 mol) was added dropwise. After addition, the solution was heated at 40° C. After 3.5 h, Na$_2$SO$_3$ (12 g, 0.095 mol) in H$_2$O (12.5 ml) was added until a negative starch iodide test was observed. The layers were separated, extracted with EtOAc (1×) and the organic layers were washed with saturated NaCl, dried, filtered and concentrated to dryness to yield 39.9 g (98%) of 11.

Step K: Preparation of 5,6-dihydro-6-(2-methoxyethoxymethyl)-4-propylamino-4H-thieno[2,3-b]thiopyran-2-sulfonamide-7,7-dioxide trans (12) and cis (13)

To a solution of 11 (39.9 g, 0.021 mol) in THF (400 ml) under N$_2$ was added dropwise 10M borane dimethylsulfide (42.5 ml, 0.42 mol). After addition, the reaction which was fitted with a short-path distillation head was heated to 60° C. for 3 h while collecting distilled dimethylsulfide and THF. The solution was then concentrated to dryness and then 6N HCl was carefully added dropwise. After addition the reaction was heated at reflux for ½ h, the solution was concentrated, flushed with EtOH (2×) and the residue was then carefully treated with saturated NaHCO$_3$. The aqueous layer was extracted with EtOAc (4×) and the organic extracts were dried, filtered and concentrated to dryness. The residue was chromatographed on a Still column (120 mm) packed with silica gel and eluted with 20:1 CHCl$_3$—CH$_3$OH to yield 15.4 g (40%) of trans -12 and then 4.7 g (12%) of cis-13.

Step L: Preparation of 2,5-Methanothieno[2,3-f]-1,4-thiazepine-7-sulfonamide-4-propyl-2,3,4,5-tetrahydro-1,1-dioxide•HCl

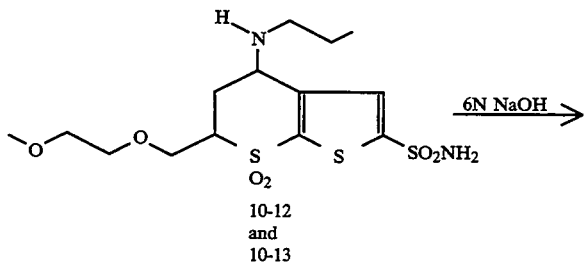

10-12 and 10-13

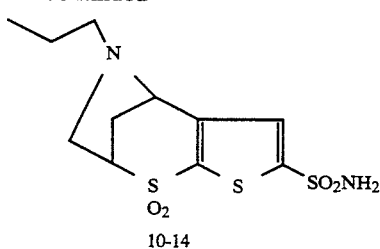

10-14 material was crystallized as the HCl salt from EtOH—HCl to yield 4.1 g (30%) of 14; mp 281°–2° C.

Anal. Calc'd for $C_{11}H_{16}N_2O_4S_3 \cdot HCl$: C, 35.43; H, 4.60; N, 7.51. Found: C, 35.51; H, 4.48; N, 7.42.

EXAMPLE 11

Cis(S,S) and cis(R,R)-2,5-methanothieno[3,2-f]-1,4-thiazepine-7-sulfonamide-4-ethyl-2,3,4,5-tetrahydro-1,1-dioxide•HCl

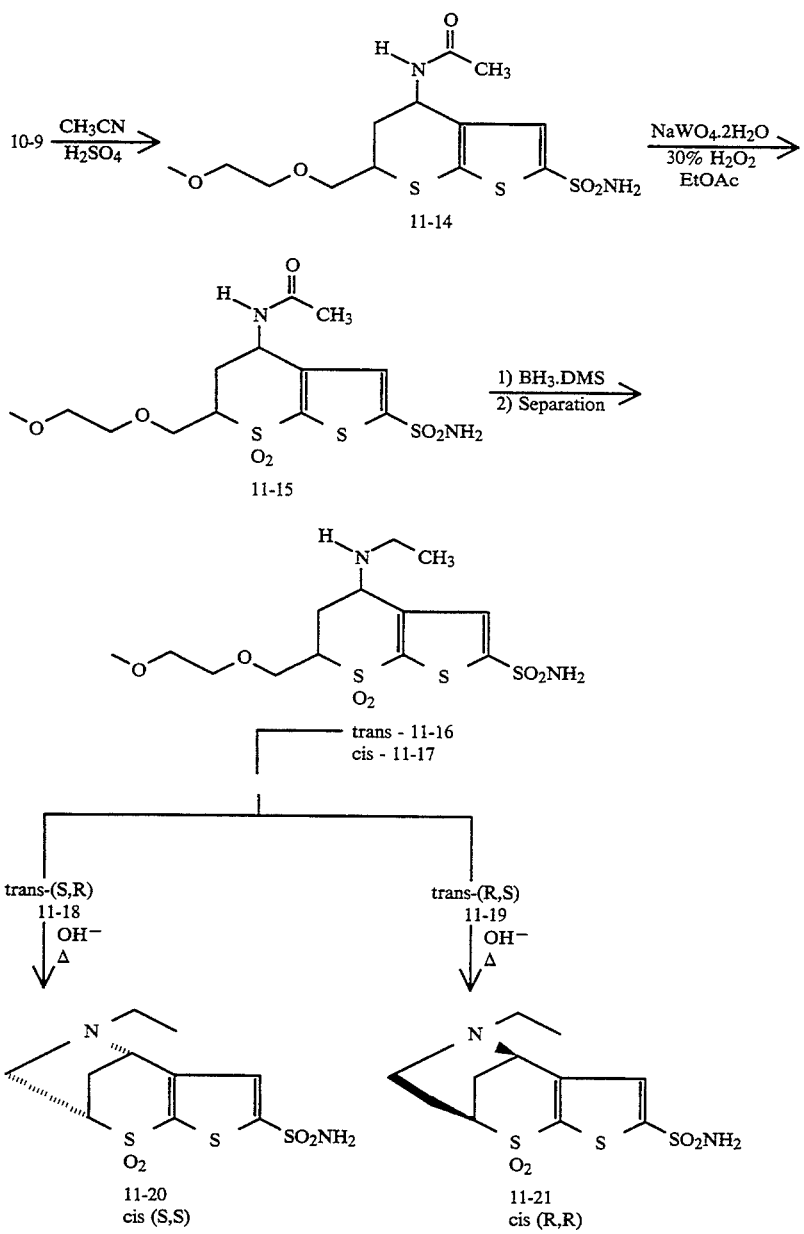

A mixture of trans(12) and cis-13 was treated with 6N NaOH (160 ml) and the solution heated at reflux. After 1.5 hours the solution was stirred at room temperature overnight. The solution was neutralized to pH 7 with 6N HCl and extracted with EtOAc (3×). The organic extracts were dried, filtered and concentrated to dryness. The residue was chromatographed on a Still column (100 mm) and the product eluted with $CHCl_3:CH_3OH$ (20:1) to yield 5.4 g of product. The Step A: Preparation of 5,6-dihydro-6-(2-methoxyethoxymethyl)-4-acetamido-4H-thieno[2,3-b]thiopyran-2-sulfonamide (14)

Compound 14 was prepared as described in Example 10-Step I, except acetonitrile was used in place of propionitrile on reaction with 9. Compound 14 was obtained in quantitiative yield.

Step B: Preparation of 5,6-dihydro-6-(2-methoxyethoxymethyl)-4-acetamido-4H-thieno[2,3-b]thiopyran-2-sulfonamide-7,7-dioxide (15)

Using the same procedure described in Example 10-Step J, compound 15 was obtained in 93% yield.

Step C: Preparation of 5,6-dihydro-6-(2-methoxyethoxymethyl)-4-acetylamino-4H-thieno[2,3-b]thiopyran-2-sulfonamide-7,7dioxide; trans-16 and cis-17

Using the same procedure described in Example 10-Step K, compounds trans-16 and cis-17 were obtained in 30% and 12% yield respectively.

Step D: Preparation of trans (S,R)-5,6-dihydro-6-(2-methoxyethoxy-methyl)-4-ethylamino-4H-thieno[2,3-b]thiopyran-2-sulfonamide-7,7-dioxide•HCl 18 and trans (R,S) 19

Trans 16 (2 g, 0.005 mol) and L-di-p-toluoyl tartaric acid (0.51 g, 0.00125 mol) was crystallized from EtOAc. The obtained solid was recrystallized 4-times more from EtOAc and then the salt was treated with saturated $NaHCO_3$. The aqueous was extracted with EtOAc (4×) and the organic extracts were dried, filtered and concentrated to dryness to yield trans (R,S). The hydrochloride salt was prepared from HCl•EtOH and recrystallized from EtOH to yield trans (S,R)-18; mp 207°-9°, $a_D^{25}$=8.9°.

Treating the mother liquor from above with saturated $NaHCO_3$ and extraction with EtOAc (6×) gave free base which when treated with D-di-p-toluoyl tartaric acid (0.51 g, 0.00125 mol) gave a new salt. Treating this new salt as described above gave trans (R,S)-19 mp 208°-10°, $a_D^{25}$=10.3°.

Step E Preparation of Cis(S,S)2,5-methanothieno-[3,2-f]-1,4-thiazepine-7-sulfonamide-4-ethyl-2,3,4,5-tetrahydro-1,1-dioxide•HCl

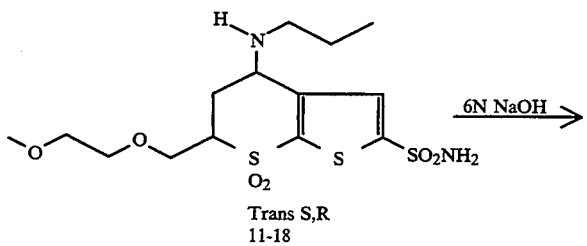

Trans S,R
11-18

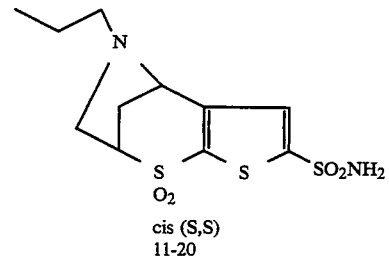

cis (S,S)
11-20

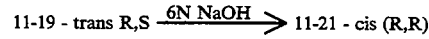

Under $N_2$, 18, trans (S,R) (0.22 g, 0.51 mmol) and 6N NaOH (5 ml) were heated at reflux. After 1.5 hours, the solution was adjusted to pH 8.5 with 6N HCl and saturated $NaHCO_3$ and the aqueous layer was extracted with EtOAc (3×). The organic layers were dried, filtered and concentrated to dryness. The residue was treated with EtOH—HCl, concentrated to dryness and crystallized from EtOH to yield 0.116 g (71%) of 20; m.p. 249°-52°; $a_D^{25}$=−21.5° (C=0.805, $CH_3OH$).

Using the same procedure described above but using 19 (trans R,S) instead of 18 (trans S,R) gave the cis (R,R) isomer 21 ; mp 249°-53°; $a_D^{25}$=21.78 (c=01505,$CH_3OH$).

EXAMPLE 12

Following the chemistry described above as well as, where needed, standard organic chemistry techniques, the following compounds also can be prepared.

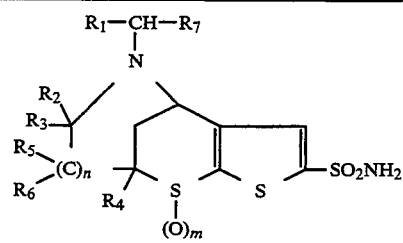

| $R_1$ | $R_1$ | $R_2$ | $R_3$ | n | $R_5$ | $R_6$ | $R_4$ | m |
|---|---|---|---|---|---|---|---|---|
| —$CH_2CH_3$ | H | H | H | 0 | — | — | H | 1 |
| —$CH_2CH(CH_3)_2$ | H | H | H | 1 | H | H | $CH_3SCH_2CH_2$— | 2— |
| —$CH_2CH_2CH_3$ | H | H | H | 1 | H | H | $CH_3SCH_2CH_2SCH_2CH_2$— | 2 |
| —$CH_2CH_3$ | H | H | H | 1 | H | H | $CH_3OCH_2CH_2SO_2CH_2CH_2$— | 2 |
| $CH_2CH_2CH_2CH_3$ | H | $CH_3$ | H | 0 | — | — | H | 2 |
| —$CH_2CH_3$ | H | H | H | 1 | $CH_3$ | — | H | 2 |
| —$CH_2CH(CH_3)_2$H | H | H | H | 1 | $CH_3CH_2$ | — | H | 2 |
| | H | H | H | 0 | — | H | H | 0 |
| —$CH_2CH_2CH_3$ | H | H | H | 1 | H | H | $CH_3CH_2NHCH_2CH_2$— | 2 |
| —$CH_2CH(CH_3)_2$ | H | H | H | 1 | H | H | $CH_3OCH_2CH_2NHCH_2CH_2$ | 2 |
| —$CH_2CH_3$ | $CH_3$ | H | H | 0 | — | — | H | 0 |
| —$CH_2CH_3$ | H | $CH_3$ | $CH_3$ | 1 | H | H | H | 2 |
| —$CH$=$CH_2$ | H | H | H | 1 | H | H | H | 2 |
| —$CH_2CH_2OCH_3$ | H | H | H | 1 | H | H | H | 2 |
| —$CH_2CH_2CH_2OH$ | H | H | H | 1 | H | H | H | 2 |
| —$CH_2CH_3$ | H | H | H | 0 | — | — | $HOCH_2CH_2$— | 2 |
| —$CH_2CH_2CH_3$ | H | H | H | 1 | H | H | $HOCH_2CH_2OCH_2$— | 2 |

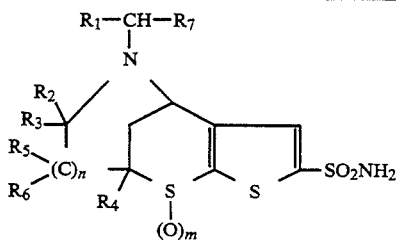

| $R_1$ | $R_1$ | $R_2$ | $R_3$ | n | $R_5$ | $R_6$ | $R_4$ | m |
|---|---|---|---|---|---|---|---|---|
| —CH₂CH₂CH₃ | H | H | H | 1 | H | H | CH=CHCH₂OCH₂— | 2 |
| —CH₂CH₂SCH₃ | H | H | H | 1 | H | H | HOCH₂CH₂SOCH₂CH₂— | 2 |
| —CH₂CH₂CH₂F | H | H | H | 1 | H | H | CH₃OCH₂CH₂CH₂— | 2 |
| —CH₂(CH₂)₂CH₃ | H | H | H | 1 | CH₃ | CH₃ | CH₃CH₂CH₂— | 2 |
| —CH₃ | H | H | H | 1 | H | H | CH₃CH₂CH₂— | 2 |
| —CH₃ | H | H | H | 0 | — | — | CH₃CH₂CH₂— | 2 |
| —CH₃ | H | H | H | 2 | H | H | CH₃CH₂CH₂ | 2 |
| —CH₂CH₃ | H | H | H | 2 | H | H | CH₃— | 2 |
| —CH₂CH₃ | H | H | H | 2 | H | H | CH₃CH₂— | 2 |
| —CH₂CH₃ | H | H | H | 2 | H | H | CH₂=CHCH₂OCH₂— | 2 |
| —CH₂CH₃ | H | H | H | 2 | H | H | CH₃OCH₂CH₂OCH₂CH₂CH₂— | 2 |

What is claimed is:

1. A compound of structural formula

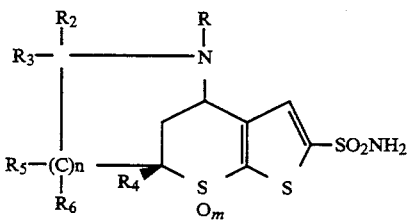

having a cis configuration, the enantiomers and mixtures thereof, or an ophthalmologically acceptable salt thereof wherein:

R is:

1) $R_1$—CH—$R_7$; or $R_1$ is:
1) H;
2) $C_{1-6}$alkyl, $C_{2-6}$alkenyl or $C_{1-6}$alkyl substituted with F, OH, $C_{1-5}$alkyl-S(O)$_m$— or $C_{1-5}$alkyl-O—;
3) phenyl or benzyl wherein the phenyl groups optionally are substituted by $C_{1-3}$alkyl, halogen, $CF_3$, OH, or $C_{1-3}$alkoxy;

$R_2$, $R_3$, $R_5$, $R_6$, and $R_7$ are independently H or $C_{1-4}$alkyl or $R_2$ and $R_3$ together are =O; and
$R_4$ is
1) H or $C_{1-6}$alkyl;
2) $C_{1-6}$alkyl substituted with
  a) hydroxy,
  b) $C_{1-3}$alkyl-O—,
  c) hydroxy-$C_{1-3}$alkyl-O—,
  d) $C_{1-3}$alkyl-O—$C_{1-3}$ alkyl-O—,
  e) hydroxy-$C_{1-3}$alkyl-O—$C_{1-3}$alkyl-O—,
  f) ($C_{1-3}$alkyl)₂-N—,
  g) hydroxy-$C_{1-3}$alkyl-NH—,
  h) $C_{1-3}$alkyl-O—$C_{1-3}$alkyl-NH—,
  i) hydroxy-$C_{1-3}$alkyl-O—$C_{1-3}$alkyl-NH—,
  j) $C_{1-3}$alkyl-S(O)$_m$—,
  k) hydroxy-$C_{1-3}$alkyl-S(O)$_m$—,
  l) $C_{1-3}$alkyl-O—$C_{1-3}$alkyl-S(O)$_m$—,
  m) hydroxy-$C_{1-3}$alkyl-O—$C_{1-3}$alkyl-S(O)$_m$—,
  n) $C_{1-3}$alkyl-S(O)$_m$-$C_{1-3}$alkyl-O—,
  o) hydroxy-$C_{1-3}$alkyl-S(O)$_m$—$C_{1-3}$alkyl-O—,
  p) $C_{1-3}$alkyl-S(O)$_m$—$C_{1-3}$alkyl-S(O)$_m$—
  q) hydroxy-$C_{1-3}$alkyl-S(O)$_m$—$C_{1-3}$alkyl-S(O)$_m$—, 3) $C_{2-3}$alkenyl or $C_{2-6}$alkenyloxy; m and n are 0, 1, or 2.

2. The compound of claim 1 wherein $R_2$, $R_3$, $R_5$, $R_6$ and $R_7$ are independently H or $C_{1-6}$alkyl; and $R_4$ is H, $C_{1-6}$alkyl or $C_{1-6}$alkyl substituted with hydroxy, $C_{1-3}$alkoxy, hydroxy-$C_{1-3}$alkoxy, $C_{1-3}$alkoxy-$C_{1-3}$alkoxy, $C_{1-3}$alkylamino or $C_{1-3}$alkoxy, $C_{1-3}$alkylamino.

3. The compound of claim 2 wherein m is 2.

4. The compound of claim 3 wherein $R_2$, $R_3$, $R_5$, $R_6$ and $R_7$ are hydrogen.

5. A compound of claim 1 wherein n is 0 and m is 0, 1 or 2.

6. A compound of claim 1 wherein n is 0 and m is 2.

7. A compound of claim 1 having the name
4-ethyl-2-[2-(2-methoxyethoxy)ethyl-2,3,4,5-tetrahydro-2,5-methanothieno[3,2-f]-1,4-thiazepine-7-sulfonamide-1,1-dioxide hydrochloride, 5-(4-methoxybenzyl)-2-methyl-3,4,5,6-tetrahydro-2H-2,6-methanothieno[3,2-g]-1,5-thiazocine-8-sulfonamide-1,1-dioxide, 5-(4-methoxybenzyl)-2-methoxypropyl-3,4,5,6-tetrahydro-2H-2,6-methanothieno[3,2-g]-1,5-thiazocine-8-sulfonamide-1,1-dioxide, 2-methyl-3,4,5,6-tetrahydro-2H-2,6-methanothieno[3,2-g]-1,5-thiazocine-8-sulfonamide-1,1-dioxide hydrochloride, 5-isobutyl-4-oxo-3,4,5,6-tetrahydro-2H-2,6-methanothieno[3,2-g]-1,5-thiazocine-8-sulfonamide, 5-isobutyl-4-oxo-3,4,5,6-tetrahydro-2H-2,6-methanothieno[3,2-g]-1,5-thiazocine-8-sulfonamide-1,1-dioxide, 5-isobutyl-3,4,5,6-tetrahydro-2H-2,6-methanothieno[3,2-g]-1,5-thiazocine-8-sulfonamide-1,1-dioxide-hydrochloride, 5-propyl-3,4,5,6-tetrahydro-2H-2,6-methanothieno[3,2-g]-1,5-thiazocine-8-sulfonamide-1,1-dioxide hydrochloride, 2,5-methanothieno[3,2-f]-1,4-thiazepine-7-sulfonamide-4-propyl-2,3,4,5-tetrahydro-1,1-dioxide•HCl, cis(S,S)2,5-methanothieno[3,2-f]-1,4-thiazepine-7-sulfonamide-4-ethyl-2,3,4,5-tetrahydro-1,1-dioxide•HCl
2methoxypropyl-3,4,5,6-tetrahydro-2H-2,6-methanothieno[3,2-g[-1,5-thiazocine.

8. A composition for the treatment of ocular hypertension comprising an ophthalmologically acceptable carrier and an effective ocular antihypertensive amount of a compound of claim 1.

9. A method of treating elevated intraocular pressure comprising the administration to a member of a mammalian species in need of such treatment of an effective intraocular pressure lowering amount of claim 1.

10. The compound of claim 1 wherein R is H.

* * * * *